United States Patent
Kim et al.

(10) Patent No.: US 10,327,723 B2
(45) Date of Patent: Jun. 25, 2019

(54) RADIATION IMAGING APPARATUS AND RADIATION IMAGE DISPLAY METHOD

(71) Applicant: SAMSUNG ELECTRONICS CO., LTD., Suwon-si, Gyeonggi-do (KR)

(72) Inventors: Ji Hye Kim, Seoul (KR); Jin Hee Park, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 497 days.

(21) Appl. No.: 14/485,007

(22) Filed: Sep. 12, 2014

(65) Prior Publication Data

US 2015/0157284 A1    Jun. 11, 2015

(30) Foreign Application Priority Data

Dec. 5, 2013 (KR) ........................ 10-2013-0150622

(51) Int. Cl.
| | |
|---|---|
| *G06F 3/0482* | (2013.01) |
| *A61B 6/00* | (2006.01) |
| *G16H 40/63* | (2018.01) |
| *G06F 19/00* | (2018.01) |

(52) U.S. Cl.
CPC .............. *A61B 6/463* (2013.01); *A61B 6/467* (2013.01); *A61B 6/502* (2013.01); *A61B 6/5235* (2013.01); *A61B 6/54* (2013.01); *G06F 3/0482* (2013.01); *G06F 19/00* (2013.01); *G16H 40/63* (2018.01); *G06F 19/321* (2013.01)

(58) Field of Classification Search
CPC ......... G06F 19/00; G06F 3/0482; G09G 5/00; A61B 6/463; A61B 6/5235
See application file for complete search history.

(56) References Cited

U.S. PATENT DOCUMENTS

| | | | | |
|---|---|---|---|---|
| 6,734,880 | B2 * | 5/2004 | Chang | A61B 6/463 |
| | | | | 715/730 |
| 2005/0047637 | A1 * | 3/2005 | Greenbaum | G06T 11/005 |
| | | | | 382/132 |
| 2008/0063250 | A1 * | 3/2008 | Ozawa | A61B 6/4441 |
| | | | | 382/132 |
| 2008/0095418 | A1 * | 4/2008 | Moriya | A61B 6/563 |
| | | | | 382/128 |

(Continued)

FOREIGN PATENT DOCUMENTS

WO    WO 01/38965    5/2001

OTHER PUBLICATIONS

Extended European Search Report dated May 15, 2015 from European Patent Application No. 14193235.0, 6 pages.

(Continued)

Primary Examiner — Rashawn N Tillery
(74) Attorney, Agent, or Firm — Staas & Halsey LLP

(57) ABSTRACT

A radiation imaging apparatus and a radiation image display method implemented using the radiation imaging apparatus, may include a display unit to display at least one first radiation image in at least one view area, and a control unit. If the control unit obtains a second radiation image corresponding to a first radiation image selected from the at least one first radiation image, the control unit controls the display unit to display the second radiation image in a view area in which the selected first radiation image is displayed.

13 Claims, 21 Drawing Sheets

(56) References Cited

U.S. PATENT DOCUMENTS

| | | | |
|---|---|---|---|
| 2009/0073473 A1* | 3/2009 | Toyoda | H04N 1/00127 358/1.9 |
| 2009/0076381 A1 | 3/2009 | Motoki et al. | |
| 2009/0226088 A1* | 9/2009 | Okazawa | G11B 27/034 382/173 |
| 2009/0232271 A1* | 9/2009 | Sendai | A61B 5/0091 378/8 |
| 2011/0236868 A1* | 9/2011 | Bronstein | G06T 19/006 434/267 |
| 2012/0288056 A1* | 11/2012 | Murakoshi | A61B 6/4233 378/37 |

OTHER PUBLICATIONS

European Office Action dated Apr. 5, 2017 from European Patent Application No. 14193235.0, 3 pages.
European Communication dated Feb. 14, 2018 in European Patent Application No. 14193235.0.
European Communication under Rule 71(3) dated Jan. 25, 2019 European Patent Application No. 14193235.0.

* cited by examiner

RADIATION IMAGING APPARATUS AND RADIATION IMAGE DISPLAY METHOD

CROSS-REFERENCE TO RELATED APPLICATIONS

This application claims the benefit of Korean Patent Application No. 10-2013-0150622, filed on Dec. 5, 2013 in the Korean Intellectual Property Office, the disclosure of which is incorporated herein by reference.

BACKGROUND

1. Field

Embodiments disclosed herein relate to a radiation imaging apparatus and a radiation image display method to generate a radiation image by emitting radiation to an object.

2. Description of the Related Art

A radiation imaging apparatus generally relates to an imaging system to obtain an image of the inside of an object by emitting radiation to the object such as a human body, animal or any other thing or object.

A radiation imaging apparatus may use a phenomenon wherein, when radiation is radiated to an object, the radiation is absorbed and attenuated by a material which is inside of the object or penetrates the material depending on the characteristics of the material or a structure thereof. As for the operation principle of the radiation imaging apparatus, after radiation is radiated to an object, such as a human body, the radiation imaging apparatus receives radiation which passes through the object without being absorbed in the object, obtains radiation signals by converting the received radiation into electric signals, and generates a radiation image.

As an example of the radiation imaging apparatus, there is provided a mammography apparatus to diagnose a breast disease. Because the breast is a body part in which mammary gland tissue and fat tissue are intermingled, in order to generate an accurate image of an internal structure of breast tissue, radiography should be performed under the condition that a breast positioned between a radiation source and a radiation detection unit is compressed by a compression paddle.

SUMMARY

It is an aspect of the disclosure to provide a radiation imaging apparatus and a radiation image display method capable of simultaneously displaying plural radiation images obtained by taking a radiograph of an object.

Additional aspects of the disclosure will be set forth in part in the description which follows and, in part, will be apparent from the description, or may be learned by practice of the invention.

In accordance with an aspect of the disclosure, a radiation imaging apparatus includes a display unit to display at least one first radiation image in at least one view area, and a control unit. If the control unit obtains a second radiation image corresponding to a first radiation image selected from the at least one first radiation image, the control unit controls the display unit to display the second radiation image in a view area in which the selected first radiation image is displayed.

The display unit may display an extension area in the view area in which the selected first radiation image is displayed. The display unit may display the selected first radiation image in the extension area. If the selected radiation image displayed in the extension area is deleted, the display unit may not display the extension area. The display unit may display a fold button, which receives an input to decide whether to display or hide the extension area, at a portion of the view area in which the extension area is generated.

The control unit may obtain the second radiation image by copying the selected first radiation image. The control unit may obtain the second radiation image by taking a radiograph of an object again so as to correspond to the selected first radiation image. The control unit may display plural first radiation images corresponding to each other in the at least one view area. The plural first radiation images corresponding to each other may include radiation images obtained by taking a radiograph of objects corresponding to each other from the same angle. The control unit may generate tags with respect to the first radiation image and the second radiation image, and may control the display unit to display the tags together with the radiation images corresponding to the tags.

The control unit may control the display unit to switch a display position of the first radiation image displayed in the extension area and a display position of the second radiation image according to a user input. The first radiation image and the second radiation image may be thumbnail images.

In accordance with another aspect of the disclosure, a radiation image display method includes displaying at least one first radiation image in at least one view area, obtaining a second radiation image corresponding to a first radiation image selected from the at least one first radiation image, and displaying the second radiation image in a view area in which the selected first radiation image is displayed.

The displaying the second radiation image may include generating an extension area in a view area in which the second radiation image is displayed. The displaying the second radiation image may further include displaying the selected first radiation image in the extension area.

The displaying the second radiation image may further include deleting the first radiation image and the extension area according to a user input. The displaying the second radiation image may further include determining whether to display the extension area according to a user input. The displaying the second radiation image may further include switching a display position of the first radiation image and a display position of the second radiation image according to a user input. The obtaining the second radiation image may include obtaining the second radiation image by copying the selected first radiation image.

The obtaining the second radiation image may include obtaining the second radiation image by taking a radiograph of an object again so as to correspond to the selected first radiation image. The displaying the first radiation image may include displaying plural first radiation images corresponding to each other in the at least one view area.

The plural first radiation images corresponding to each other may include plural radiation images obtained by taking a radiograph of objects corresponding to each other from the same angle.

The displaying the first radiation image may include generating a tag of the at least one first radiation image, and displaying the generated tag and the at least one first radiation image.

The displaying the second radiation image may include generating a tag of the second radiation image so as to be discriminated from the tag of the first radiation image.

In accordance with another aspect of the disclosure, a radiation imaging apparatus includes a display unit to display radiation images, a radiography module, a radiation module driving unit to rotate the radiography module, and a control unit. The radiography module may include a radiation source to emit radiation toward an object, and a radiation detector to detect radiation passing through the object and to output electric signals corresponding to the detected radiation. The control unit may control the radiation module driving unit to control rotation of the radiography module to obtain radiation images of the object at different angles, control the radiation source to emit radiation toward the object, obtain the plurality of radiation images based on the electric signals output by the radiation detector, and control the display unit to display the plurality of radiation images. The display unit may display a plurality of view areas including a first view area which includes a first radiation image of the object obtained at a first angle, and a second view area which includes a second radiation image of the object obtained at a second angle.

The display unit may display a menu area including a plurality of icons used to control operations of the radiation imaging apparatus. In response to selection of the first radiation image and a first icon displayed in the menu area, the control unit may control the radiation imaging apparatus to recapture a radiation image corresponding to the first radiation image by rotating the radiography module to the first angle. The control unit may generate a first extension area in the first view area, and control the display unit to display the recaptured radiation image in the first view area, and display the first radiation image in the first extension area.

In response to selection of the recaptured radiation image and a second icon displayed in the menu area, the control unit may control the radiation imaging apparatus to copy the recaptured radiation image. The control unit may generate a second extension area in the first view area, and control the display unit to display the copy of the recaptured radiation image in the first view area, display the recaptured radiation image in the first extension area, and display the first radiation image in the second extension area.

The control unit may generate different markers for the copy of the recaptured radiation image, the recaptured radiation image, and the first radiation image, the markers being displayed at predetermined positions of the respective radiation images.

In response to selection of a third icon displayed in the menu area, the control unit may control the radiation imaging apparatus to add a pre-stored radiation image to a view area.

As apparent from the above description, the radiation imaging apparatus enables an operator to efficiently analyze plural radiation images by displaying the plural related radiation images in one view area.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
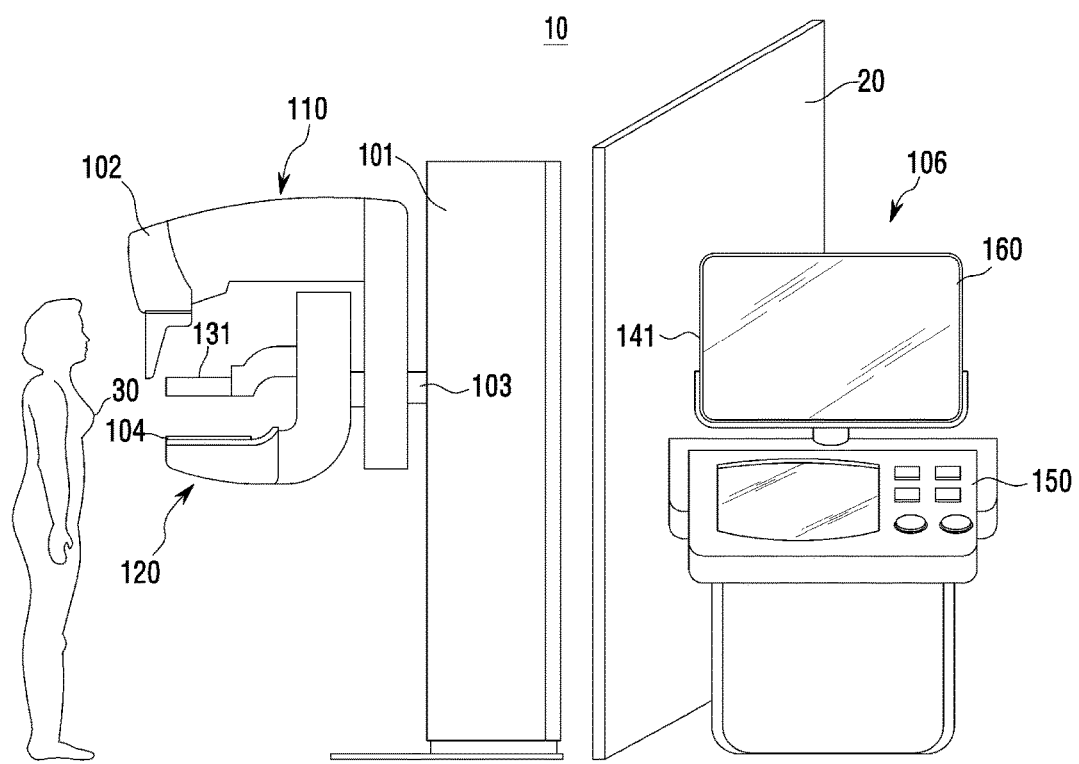
FIG. 1 is a perspective view illustrating an external appearance of a radiation imaging apparatus according to an exemplary embodiment of the disclosure.

Reference will now be made in detail to the embodiments of the disclosure, examples of which are illustrated in the accompanying drawings, wherein like reference numerals refer to like elements throughout.

A radiation imaging apparatus according to an exemplary embodiment of the disclosure is configured to (arranged to, adapted to, capable of, suitable for, etc.) obtain plural radiation images of an object and display the obtained plural radiation images to a user. Particularly, the radiation imaging apparatus may display plural related radiation images in the same view area.

Hereinafter, a radiation imaging apparatus according to an exemplary embodiment of the disclosure will be described by way of an example of a mammography apparatus, however, embodiments are not limited thereto. The radiation imaging apparatus according to the embodiment may include any kind of radiation imaging apparatus capable of displaying plural related radiation images in the same view area.

FIG. 1 is a perspective view illustrating an external appearance of a radiation imaging apparatus according to an exemplary embodiment of the disclosure. An object 30 for the radiation imaging apparatus depicted in FIG. 1 may correspond to a breast.

For example, as illustrated in FIG. 1, a radiography module 102 may be configured to (arranged to, adapted to, capable of, suitable for, etc.) emit radiation to an object 30 positioned between a radiation generation unit 110 and a radiation detection unit 120, detect the radiation which passes through the object 30 and obtain a radiation image of the object 30. Here, the object 30 may correspond to a patient's breast, as an example.

A portion of the radiography module 102 may be coupled to a connection arm 103 so as to be supported by a housing 101. The radiography module 102 coupled to the connection arm 103 may be rotated, which will be explained in detail below.

The radiography module 102 may further include a compression unit 130 disposed between the radiation generation unit 110 and the radiation detection unit 120. The compression unit 130 may be configured to (arranged to, adapted to, capable of, suitable for, etc.) move up and down to compress the object 30 placed on an object platform 104. Because a breast, which is the object 30, is composed of soft tissue, a clearer radiation image is obtained by compressing the breast. In addition, when the breast is compressed, a thickness of the object 30 is decreased and thus radiation exposure of the object 30 is decreased.

A host device 106 may include a display unit 160 to display a radiation image and an input unit 150 to receive commands for operation of the radiation imaging apparatus 10. The radiation imaging apparatus 10 may further include a shielding panel 20 to separate an area where the host device is manipulated from an area where a radiograph is taken, in order to prevent unnecessary radiation exposure to a user of the radiation imaging apparatus 10. The shielding panel 20 may be made of a material capable of (arranged to, adapted to, configured to, suitable for, etc.) absorbing radiation, such as lead or the like. The display unit 160, input unit 150, and/or the radiation generation unit 110, may be connected to one another over a wired or wireless network, or a combination thereof.

The radiation imaging apparatus 10 depicted in FIG. 1 is illustrative only, and may have various other external appearances and constitutions.

Figure 2:
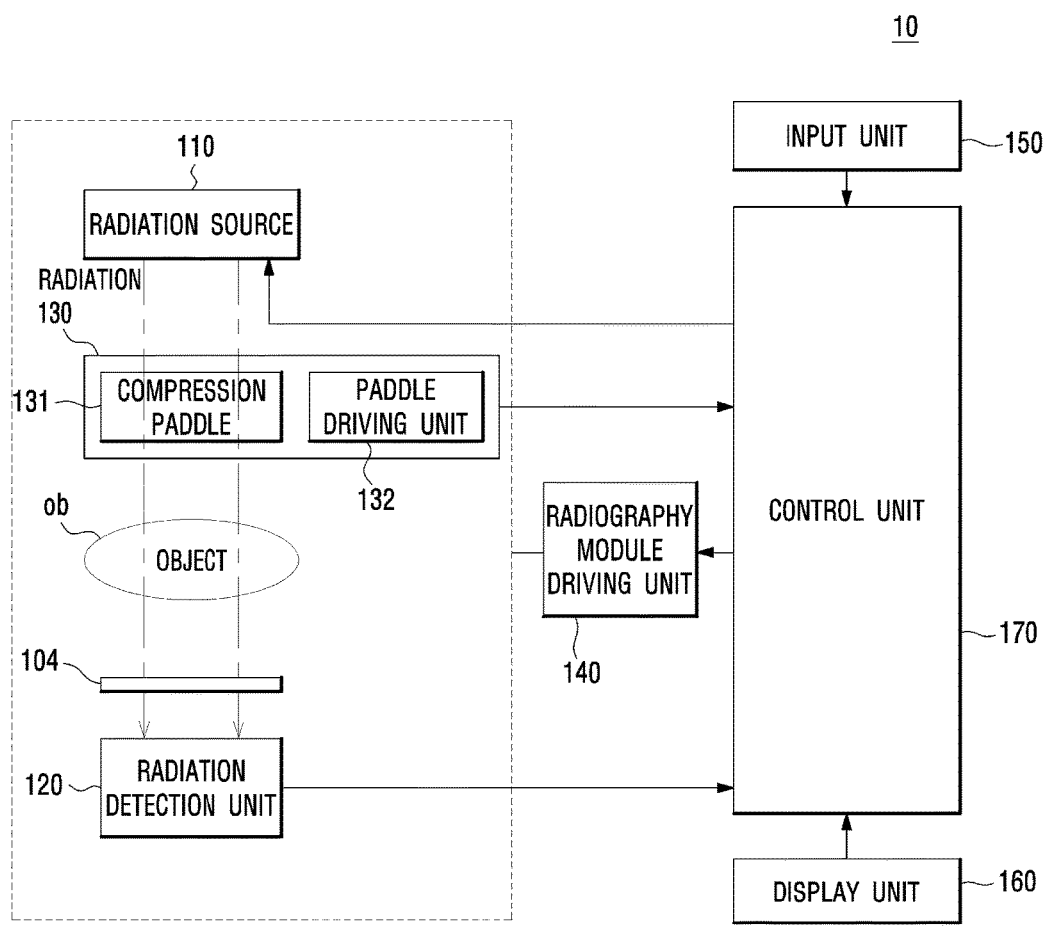
FIG. 2 is a control block diagram to explain the radiation imaging apparatus according to the exemplary embodiment of the disclosure in detail.

FIG. 2 is a control block diagram to explain the radiation imaging apparatus according to the exemplary embodiment of the disclosure in detail.

The radiation imaging apparatus 10 may include a radiography module 102 to emit radiation to the object 30 and output electric signals by detecting the radiation which passes through the object 30, a radiography module driving unit 140 to rotate the radiography module 102, an input unit 150 to receive user commands for operation of the radiation imaging apparatus 10, a display unit 160 to display an image related to the radiation imaging apparatus, and a control unit 170 (controller) to control overall operation of the radiation imaging apparatus 10. The radiography module 102 may include a radiation generation unit (radiation source) 110 to generate radiation, a compression unit 130 to compress a breast which is the object 30 (abbreviated ob in FIG. 2), and a radiation detection unit 120 to detect the radiation which passes through the object 30. The compression unit 130 may include a compression paddle 131 which may be configured to (arranged to, adapted to, capable of, suitable for, etc.) come into contact with the object 30 and a paddle driving unit 132 to move the compression paddle 131 up and down.

An example of the radiation generation unit 110 of the radiation imaging apparatus will be explained hereinafter.

Figure 3:
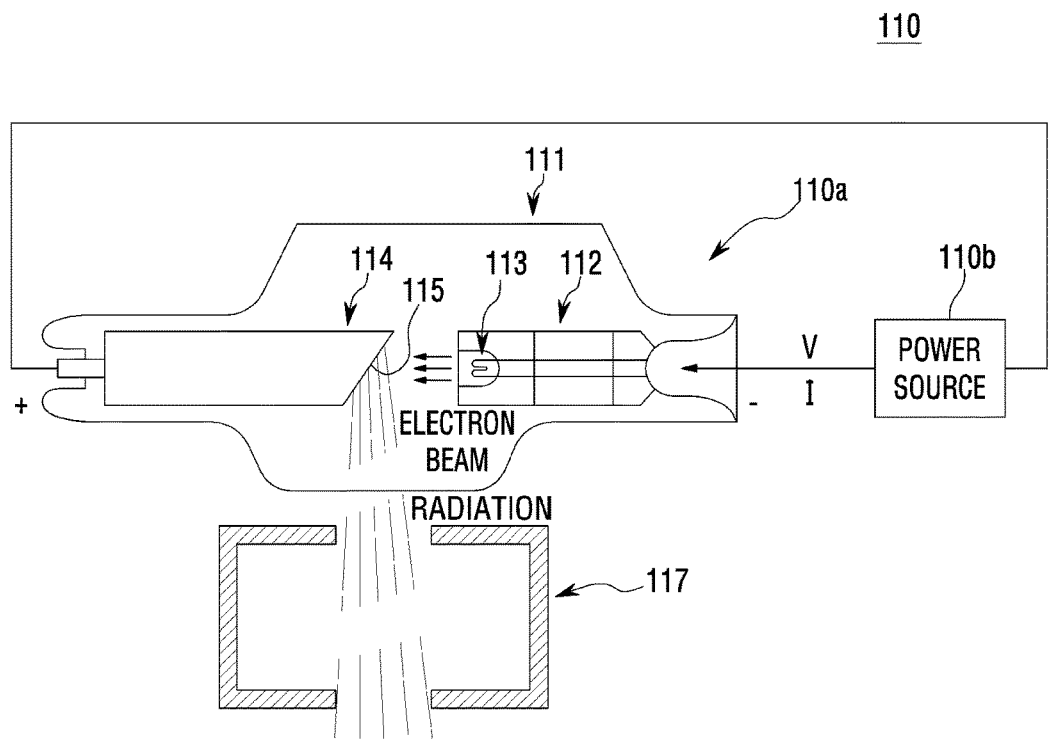
FIG. 3 is a view schematically illustrating an example of a radiation generation unit.

FIG. 3 is a view schematically illustrating an example of the radiation generation unit 110.

The radiation generation unit 110 of the radiation imaging apparatus 10 may be configured to (arranged to, adapted to, capable of, suitable for, etc.) generate radiation having a predetermined energy and emit the generated radiation in a predetermined direction, for example, toward the object 30. In particular, as shown in FIG. 3, the radiation generation unit 110 may include a radiation tube 110a to generate radiation and a power source 110b to apply a voltage to the radiation tube 110a.

The radiation tube 110a may include a tubular body 111 to contain other components therein, a cathode 112 and an anode 114. The cathode 112 may be provided with a filament 113 in which electrons gather, and the anode 114 may be provided with a target 115 with which the electrons generated from the filament 113 collide and are decelerated.

The tubular body 111 may be a glass tube made of silicate glass. The tubular body 111 may be structured such that the cathode 112 and the anode 114 are stably fixed in the tubular body 111 and the degree of vacuum in the tube is maintained at a high value of about $10^{-7}$ mmHg.

The filament 113 of the cathode 112 is connected to the power source 110b so that the filament 113 is heated by a tube voltage applied by the power source 110b and discharges electrons having a predetermined energy into the tubular body 111. The filament 113 of the cathode may be made of tungsten (W). The cathode 112 may include a focusing electrode to focus the discharged electrons as needed. Alternatively, a carbon nano-tube may be used in the cathode 112 instead of the filament 113.

The electrons discharged from the filament 113 of the cathode 112 may be accelerated in the tubular body 111 and move toward the anode 114. The accelerated electrons moving toward the anode 114 collide with the target 115 provided at the anode 114 and are decelerated rapidly by Coulomb force. When the electrons are decelerated, radiation having an energy corresponding to the applied tube voltage is generated according to the law of conservation of energy.

As illustrated in FIG. 3, the anode 114 may be a fixed electrode. The fixed anode 114 may have a cut surface which is cut by a predetermined angle, and may be formed with the target 115 at the cut surface thereof, with which the accelerated electrons discharged from the filament 113 collide. In this case, a cutting angle of the fixed anode 114 may be about 20 degrees with respect to an axis of the tube in a vertical direction. The target 115 may be formed with a focal point as a collision surface with which the accelerated electrons collide. The focal point may have a rectangular shape. By collision of the accelerated electrons, a predetermined amount of radiation may be discharged from the focal point.

The anode 114 may be made of a metal such as copper or the like. The target 115 may be made of a metal such as tungsten (W), chrome (Cr), iron (Fe), nickel (Ni) or the like.

Although not illustrated in the drawings, according to another exemplary embodiment, the anode may be formed in a rotatable disc shape. In this case, the anode may rotate about an axis along which the accelerated electrons move. The anode may rotate at about 3,600 through about 10,800 revolutions per minute. A boundary surface of the disk of the anode may be cut by a predetermined angle. Similar to the above description, the cut portion of the boundary surface of the disc may be formed with a target with which the electrons discharged from the filament collide. The anode may be rotated by a rotor coupled thereto, and the target may also be rotated by rotation of the anode. If the target is rotated by rotation of the anode, effects of increase in the degree of heat accumulation and decrease in the size of focal point may be obtained in comparison with the fixed anode. Further, acquisition of a clearer radiation image may be achieved.

If radiation is generated from the anode 114, the generated radiation may be emitted in a predetermined direction, for example, toward the object 30. In this case, a collimator 117 may be provided in the emission path of the radiation.

The collimator 117 may be configured to (arranged to, adapted to, capable of, suitable for, etc.) filter a stream of radiation by allowing only the radiation traveling parallel to a specified direction to pass therethrough and absorbing or reflecting the radiation travelling non-parallel to the specified direction. Such a collimator 117 makes it possible for the radiation generation unit 110 to emit the radiation within a certain range or in a certain direction. The collimator 117 may be made of a material capable of (arranged to, adapted to, configured to, suitable for, etc.) absorbing radiation, such as lead (Pb) or the like.

Alternatively, the embodiment may be constituted such that the radiation penetrates a certain filter after passing through the collimator 117. In this case, the filter may be made of aluminum (Al), copper (Cu) or the like. The filter may function to attenuate the radiation passing through the collimator 117 by a certain degree.

The power source 110b may be configured to (arranged to, adapted to, capable of, suitable for, etc.) apply a certain voltage, i.e., tube voltage, to the anode 114 and the cathode 112 of the radiation tube 110, thereby adjusting the radiation energy discharged from the anode 114.

The radiation generation unit 110 may be configured to (arranged to, adapted to, capable of, suitable for, etc.) control the radiation energy and intensity according to the tube voltage and tube current applied to the radiation tube 110 by the power source and a radiation exposure time.

Hereinafter, an example of the radiation detection unit 120 of the radiation imaging apparatus will be described.

Figure 4:
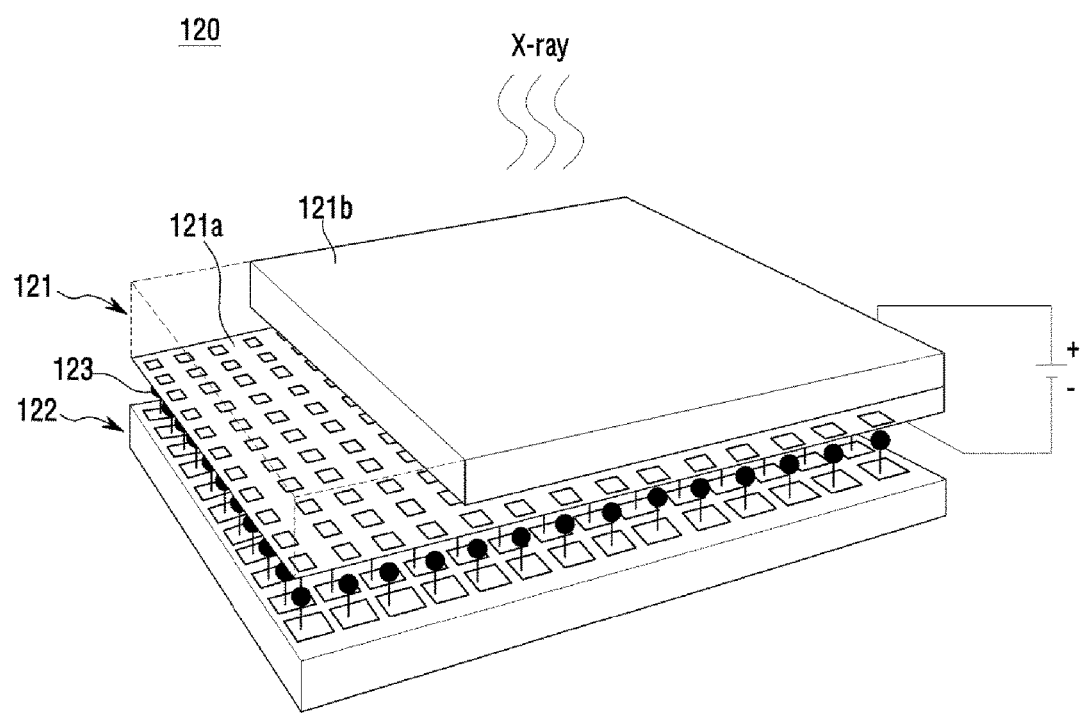
FIG. 4 is a view schematically illustrating an example of a radiation detection unit.

FIG. 4 is a view schematically illustrating an example of the radiation detection unit 120. The radiation detection unit may include a radiation detector. The radiation detector represents a device that detects the radiation passing through the object 30 and outputs electric signals corresponding to the detected radiation. The radiation detector may be classified according to material composition, a method of converting the detected radiation into electric signals and a method of obtaining image signals.

The radiation detector may be classified into a detector constituted by a monolithic type element and a detector constituted by hybrid type elements according to material composition.

The radiation detector of a monolithic type element may be constituted such that both a part to detect radiation and generate electric signals and a part to read and process the electric signals are formed by a semiconductor of a monolithic material or manufactured by a monolithic process. For example, a charge coupled device (CCD) or a complementary metal oxide semiconductor (CMOS), which is a light receiving element, is commonly used.

The radiation detector of hybrid-type elements is constituted such that a part to detect radiation and generate electric signals and a part to read and process the electric signals may be formed by different elements or manufactured by different processes. For example, radiation may be detected by a light receiving element, such as a photodiode, CdZnTe or the like, and electric signals are read and processed by a CMOS readout integrated circuit (ROIC). Alternatively, radiation may be detected by a strip detector, and electric signals are read and processed by a CMOS ROIC. Further alternatively, an a-Si or a-Se flat panel system may be used.

The radiation detector may also be classified into a direct conversion mode and an indirect conversion mode according to a method of converting radiation into electric signals.

In the direct conversion mode, if radiation is emitted, electron-hole pairs are temporarily generated in the light receiving element, and the electrons move to the anode and the holes move to the cathode by an electric field applied to both ends of the light receiving element. The radiation detector converts such movement into electric signals. In the direct conversion mode, a material used for the light receiving element may include a-Se, CdZnTe, $HgI_2$, $PbI_2$ or the like.

In the indirect conversion mode, a scintillator is provided between the light receiving element and the radiation source. Radiation emitted from the radiation source reacts to the scintillator and photons having a wavelength of visible light are emitted. The light receiving element detects the photons and converts the same into electric signals. In the indirect conversion mode, a material used for the light receiving element may include a-Si or the like, and the scintillator may be embodied as a thin-film type GADOX scintillator, or a micro-column type or needle structured type CSI (T1) scintillator.

Additionally, according to a method of obtaining image signals, the radiation detector may be classified into a charge integration mode in which charges are stored for a certain time and then signals are obtained, and a photon counting mode in which photons having energy greater than a threshold energy are counted whenever signals are generated by a photon of radiation.

The radiation imaging apparatus 10 according to the example embodiments of the disclosure may use any one of the above-described various types of radiation detector. Further, the example embodiments disclosed herein are not limited to the above-described types, and any other method of detecting radiation, converting the radiation into electric signals and obtaining image signals may be used.

For concrete explanation, a radiation detection unit including a radiation detector employing a direct conversion mode of directly obtaining electrical signals from radiation and a hybrid-type constitution of combining a light receiving element to detect radiation and a readout circuit chip will now be described.

Referring to FIG. 4, the radiation detection unit 120 may include a light receiving element 121 to detect radiation and convert the radiation into electric signals, and a readout circuit 122 to read the electric signals. The readout circuit 122 may be configured as (arranged as, adapted as, capable of being, suitable as, etc.) a two-dimensional pixel array including plural pixel regions. A single crystal semiconductor material may be used as the light receiving element 121 in order to secure high resolution, rapid response time and high dynamic range at low energy and low dose. The single crystal semiconductor material may include Ge, CdTe, CdZnTe, GaAs or the like.

The light receiving element 121 may be configured as (arranged as, adapted as, capable of being, suitable as, etc.) a PIN photodiode in which a p-type layer 121b having a two-dimensional pixel array arrangement of a p-type semiconductor is bonded to a bottom surface of a high-resistance n-type semiconductor substrate 121a. The readout circuit 122 using a CMOS process may be combined with the light receiving element 121 pixel by pixel. The CMOS readout circuit 122 and the light receiving element 121 may be combined through a flip chip bonding process. A bump 123 made of solder (PbSn), indium (In) or the like is first formed, and the CMOS readout circuit 122 and the light receiving element 121 are pressed against each other while performing reflow soldering and applying heat. Such a structure of the radiation detection unit is merely illustrative, and is not limited to the above-described structure.

Referring back to FIGS. 1 and 2, the compression unit 130 may include a compression paddle 131 which is configured to (arranged to, adapted to, capable of, suitable for, etc.) come into contact with the object 30 and a paddle driving unit 132 to move the compression paddle 131 up and down. The paddle driving unit 132 may move the compression paddle 131 up and down for radiography.

For example, if the object 30 is placed on the object platform 104, the paddle driving unit 132 moves the compression paddle 131 toward the object 30 so that the compression paddle 131 compresses the object 30. At this time, the paddle driving unit 132 may move the compression paddle 131 up and down by user manipulation or may automatically move the compression paddle 131 according to a preset condition. The compression unit 130, which operates such that the compression paddle 131 is automatically moved according to a preset condition, may further include a sensor capable of detecting contact with the object 30 and measuring pressure applied to the object 30. Additionally, the paddle driving unit 132 may include a motor to supply force to the compression paddle 131.

The radiography module driving unit 140 may rotate the radiography module 102. In general, a mammography apparatus may obtain plural radiation images by taking a radiograph of a breast, which corresponds to the object 30 in an example embodiment, from plural angles. In order to take a radiograph of a breast from plural angles, the radiography module 102 is rotated.

For example, the radiography module driving unit 140 may rotate the radiography module 102 according to control of the control unit 170. As shown in FIG. 1, in a case that the connection arm 103 and the radiography module 102 are coupled to each other, the radiography module driving unit 140 may rotate the connection arm 103, to thereby rotate the radiography module 102 coupled to the connection arm 103. The radiography module driving unit 140 may be provided in the housing, and may include a motor to generate rotational torque. The motor may be a stepping motor capable of rotational angle control, for example. The above-described radiography module driving unit 140 is just an illustrative example to rotate the radiography module 102, and embodiments are not limited thereto. For example, the radiography module 102 may have a built-in device to rotate the radiography module 102, or may be constituted such that only a part of the radiography module 102 is rotated.

The input unit 150 may be configured to (arranged to, adapted to, capable of, suitable for, etc.) receive a command input by a user for operation control of the radiation imaging apparatus 10, generate electric signals according to the user command and transmit the electric signals to the control unit 170. The input unit 150 may be embodied as various input devices. For example, the input unit may include, one or more of a keyboard, a mouse, a joystick, a button, a switch, an electronic pen or stylus, an input sound device (e.g., a microphone to receive a voice command), a camera to capture a gesture (e.g., movement of a body part), an output sound device (e.g., a speaker), a track ball, a remote controller, a portable (e.g., a cellular or smart) phone, a tablet PC, a pedal or footswitch, a virtual-reality device, and so on. The input unit may further include a haptic device to provide haptic feedback to a user. The input unit may also include a touchscreen, for example.

The display unit 160 may be configured to (arranged to, adapted to, capable of, suitable for, etc.) display various information related to the radiation imaging apparatus 10. The display unit 160 may be embodied as one or more display devices 141, and may include a liquid crystal display (LCD), light emitting diode (LED), organic light emitting diode (OLED), active matrix organic light emitting diode (AMOLED), flexible display, 3D display, plasma display panel (PDP), a cathode ray tube (CRT) display, or the like.

The display unit 160 may also be embodied as a touchscreen capable of performing total (all of) or partial (some of) functions of the input unit 150. Hereinafter, an embodiment of the display unit 160 that is embodied as a touchscreen so as to display plural radiation images and also partially perform functions of the input unit 150 by user touch, will be described. The display unit 160 and/or input unit 150 may include a plurality of connectors such as USB 2.0, USB 3.0, HDMI, IEEE 1394, or the like, to be connected to various types of input devices or user interfaces by a wired connection. Alternatively, or in addition to a wired connection, the display unit 160 and/or input unit 150 may be connected to various types of input devices or user interfaces via a wireless connection. The wireless connection may be performed using various types of wireless networks, for example via BLUETOOTH or WI-FI, or via a remote control device such as by using an infrared remote control, for example.

The control unit 170 generally controls the radiation imaging apparatus 10 so that the radiation imaging apparatus 10 obtains radiation images and displays the obtained radiation images on the display unit 160.

The control unit 170 may be embodied as one or plural processors. The processor may be implemented as an array of a plurality of logic gates, or may be implemented as a combination of a general microprocessor and a memory where a program to be executed by the microprocessor is stored. For example, the one or more processors may include an arithmetic logic unit, a central processing unit (CPU), a graphics processing unit (GPU), a digital signal processor (DSP), a microcomputer, a field programmable array, a programmable logic unit, an application-specific integrated circuit (ASIC), or any other device capable of responding to and executing instructions in a defined manner. It will be also understood by those skilled in the art that the processor may be implemented as another form of hardware.

The control unit 170 may control the radiography module 102 and the radiography module driving unit 140 in order to obtain plural radiation images with respect to the object 30. The control unit 170 may control the radiation generation unit 110 to emit radiation toward the object 30, control the radiation detection unit 120 to detect the radiation passing through the object 30, and obtain a radiation image by receiving electric signals generated from the radiation detection unit 120.

For example, the control unit 170 may obtain a radiation image based on the electric signals transmitted from the radiation detection unit 120. For example, the control unit 170 may obtain a radiation image in which a relatively bright color represents a region corresponding to a pixel of strong electric signals and a relatively dark color represents a region corresponding to a pixel of weak electric signals.

Further, the control unit 170 may control the radiography module driving unit 140 to rotate the radiography module 102, thereby obtaining plural radiation images with respect to the object 30. A process of obtaining plural radiation images will now be explained in detail with reference to FIGS. 5A to 5C.

Figure 5A:
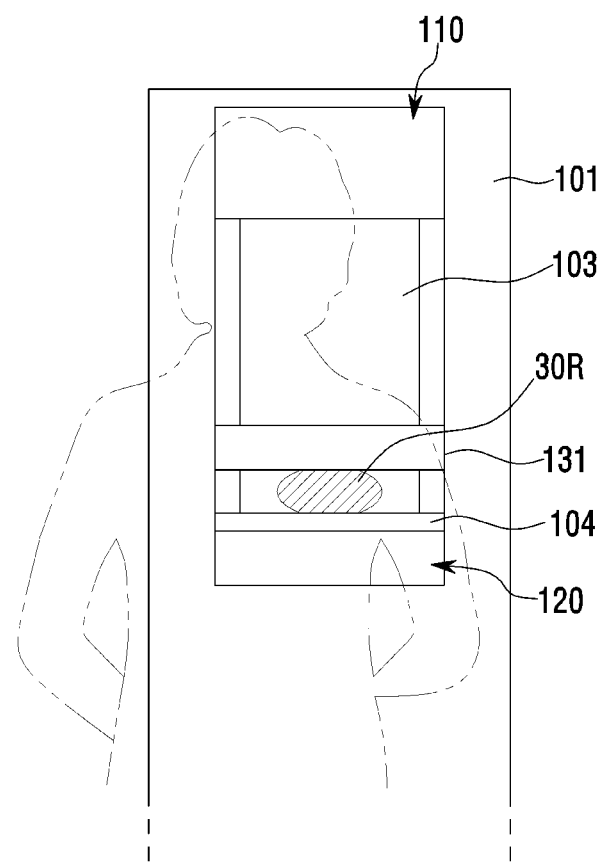
FIGS. 5A to 5C are views to explain a radiation acquisition process of the radiation imaging apparatus according to the exemplary embodiment of the disclosure in detail.
Figure 5B:
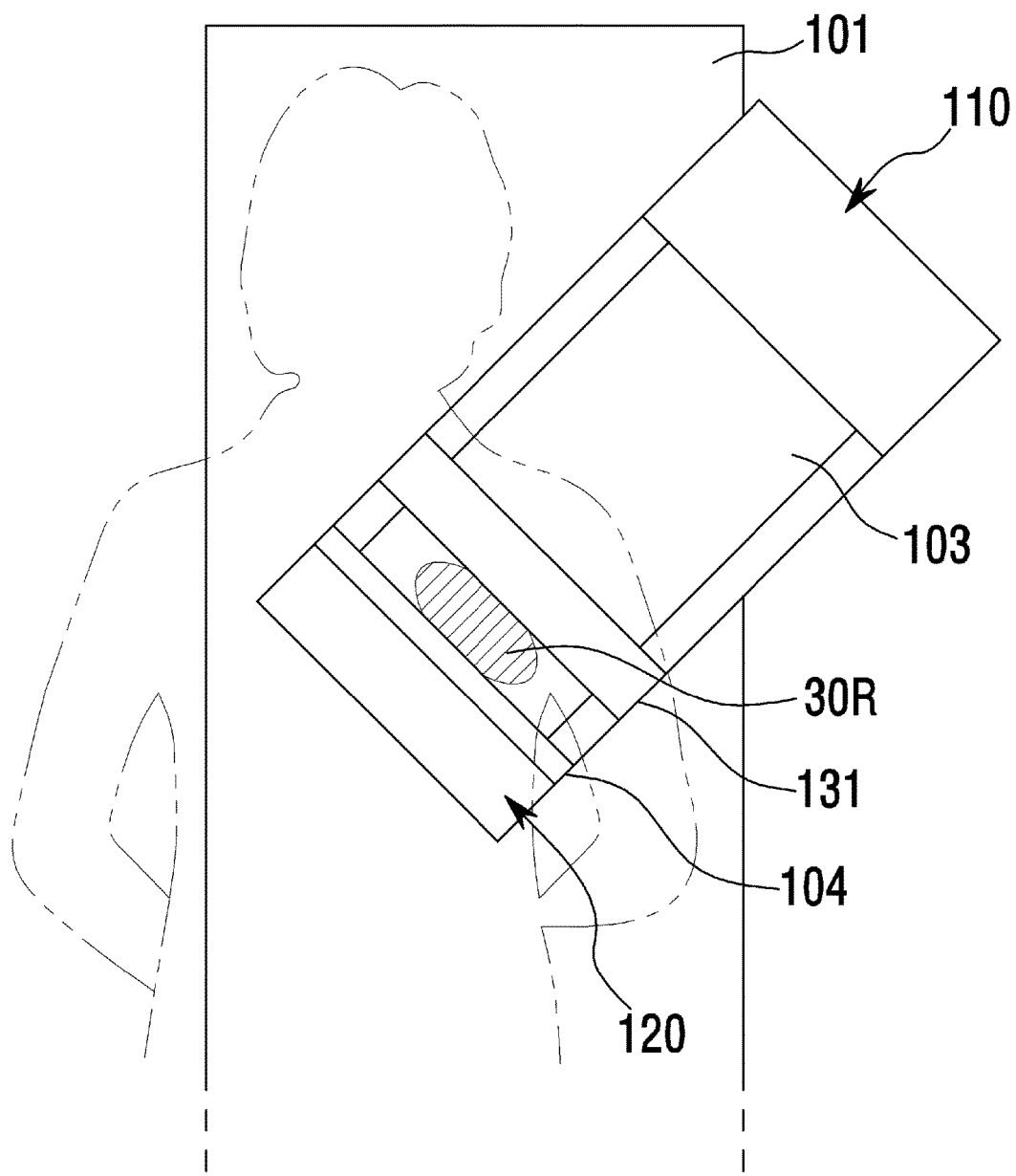
Figure 5C:
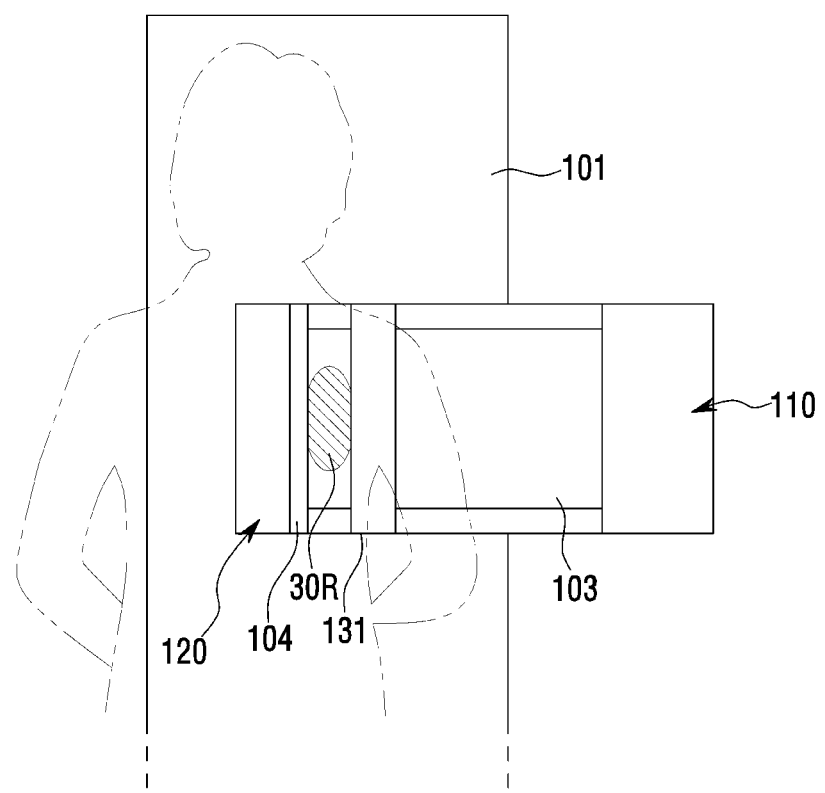

FIGS. 5A to 5C are views to explain a process of obtaining radiation images in the radiation imaging apparatus according to an example embodiment of the disclosure, in detail. FIG. 5A is a view schematically illustrating the radiation imaging apparatus to explain taking a craniocaudal radiation image of a right breast. FIG. 5B is a view schematically illustrating the radiation imaging apparatus to explain taking a mediolateral oblique radiation image of a right breast. FIG. 5C is a view schematically illustrating the radiation imaging apparatus to explain taking a mediolateral radiation image of a right breast. Hereinafter, a right breast is denoted by reference numeral 30R, and a left breast is denoted by reference numeral 30L.

As illustrated in FIG. 5A, the control unit 170 places the radiography module 102 in parallel with the housing 101, controls the object platform 104 and the compression paddle 131 to compress the right breast 30R, takes a radiograph of the compressed right breast 30R in a craniocaudal direction, and obtains a craniocaudal radiation image of the right breast 30R (i.e., a right craniocaudal view; hereinafter, referred to as an RCC view). The craniocaudal direction may be in a direction parallel to a greater pectoral muscle.

After obtaining the RCC radiation image, the control unit 170 moves the compression paddle 131 upward and, as shown in FIG. 5B, rotates the radiography module 102 clockwise by a predetermined angle (for example, 45 degrees).

Then, the control unit 170 moves the compression paddle 131 toward the object platform to compress the right breast 30R, takes a radiograph of the compressed breast in a mediolateral oblique direction, and obtains a mediolateral oblique radiation image of the right breast 30R (i.e., a right mediolateral oblique view; hereinafter, referred to as an RMLO view). The mediolateral oblique direction may be in a direction which forms a predetermined angle with a greater pectoral muscle.

After obtaining the RMLO radiation image, the control unit 170 moves the compression paddle 131 in the opposite direction to the object platform 104 and, as shown in FIG. 5C, rotates the radiography module 102 clockwise by a predetermined angle (for example, 45 degrees).

Then, the control unit 170 again moves the compression paddle 131 toward the object platform 104 to compress the right breast 30R, takes a radiograph of the compressed breast in a mediolateral direction, and obtains a mediolateral radiation image of the right breast 30R (right mediolateral view; hereinafter, referred to as RML view). The mediolateral direction may be a direction perpendicular to a greater pectoral muscle.

The above-described method of obtaining a radiation image mayl also identically be applied to the left breast 30L. Accordingly, the control unit 170 may obtain a craniocaudal radiation image of the left breast 30L (i.e., a left craniocaudal view; hereinafter, referred to as an LCC view), a mediolateral oblique radiation image of the left breast 30L (i.e., a left mediolateral oblique view; hereinafter, referred to as an LMLO view) and a mediolateral radiation image of the left breast 30L (i.e., left mediolateral view; hereinafter, referred to as an LML view). Thus, a total of six images may be obtained (three for the left breast and three for the right breast).

The above-described process of obtaining a radiation image is just an illustrative example to obtain plural radiation images, and embodiments are not limited thereto. An order of obtaining plural radiation images may be changed. For example, the control unit 170 may obtain radiation images in the order of RCC view, LCC view, RMLO view, LMLO view, RML view and LML view. The number of the obtained radiation images may also be changed, and may be more than three images or less than three images for each breast. For example, the control unit 170 may obtain only a craniocaudal view and a mediolateral view, or may additionally obtain a radiation image from a specified angle according to a user input or a preset program. The number of images obtained for each breast may be the same, or may be different.

The control unit 170 may display the radiation image obtained as described above on the display unit 160. At this time, at least one radiation image may be displayed on the display unit 160. In addition, the control unit 170 may generate plural thumbnail images corresponding to plural radiation images, and may display the generated thumbnail images on the display unit 160. As such, the control unit 170 may convert the plural radiation images into thumbnail images and display the same, thereby enabling a user to check the plural radiation images simultaneously.

Additionally, the control unit 170 may control the display unit 160 so that one or more view areas are displayed on the display unit 160. The number of view areas may be decided by a user or may be predetermined. The view areas may be displayed adjacent to each other.

One or more radiation images may be displayed in the view area. For example, the radiation images corresponding to each other (for example, the radiation image of the right breast 30R and the radiation image of the left breast 30L taken from the same angle) may be displayed in one view area. In order to achieve this, the control unit 170 may classify the plural radiation images according to a preset criterion or a criterion set by a user so that the view areas in which the respective radiation images are displayed are determined. If the classification of the radiation images is changed by a user, the radiation images may be displayed in the corresponding view areas according to the changed classification, which will be explained in detail below.

By displaying the radiation images corresponding to each other in one view area, a user is enabled to more easily discriminate and observe the plural radiation images. Further, a radiation imaging operation may be facilitated.

In addition, the control unit 170 may generate tags of the respective radiation images, and may display the radiation images together with the tags. The tags may be generated without being overlapped, and thus may be used as identifiers of the respective radiation images. By displaying the radiation images together with the tags, the radiation imaging apparatus 10 may enhance discrimination between the radiation images. The tags may include various information including object identification information (e.g., a name of the patient, name of the body part, etc.), attributes of the image taken (e.g., an angle at which the image was taken, date, time of day, resolution, size, etc.), and the like. The tags may alternatively be overlaid on the radiation image, and may be transparently overlaid. Thus, additional space on the display may be used to show the radiation images while still including respective tags to identify the radiation images.

Figure 6A:
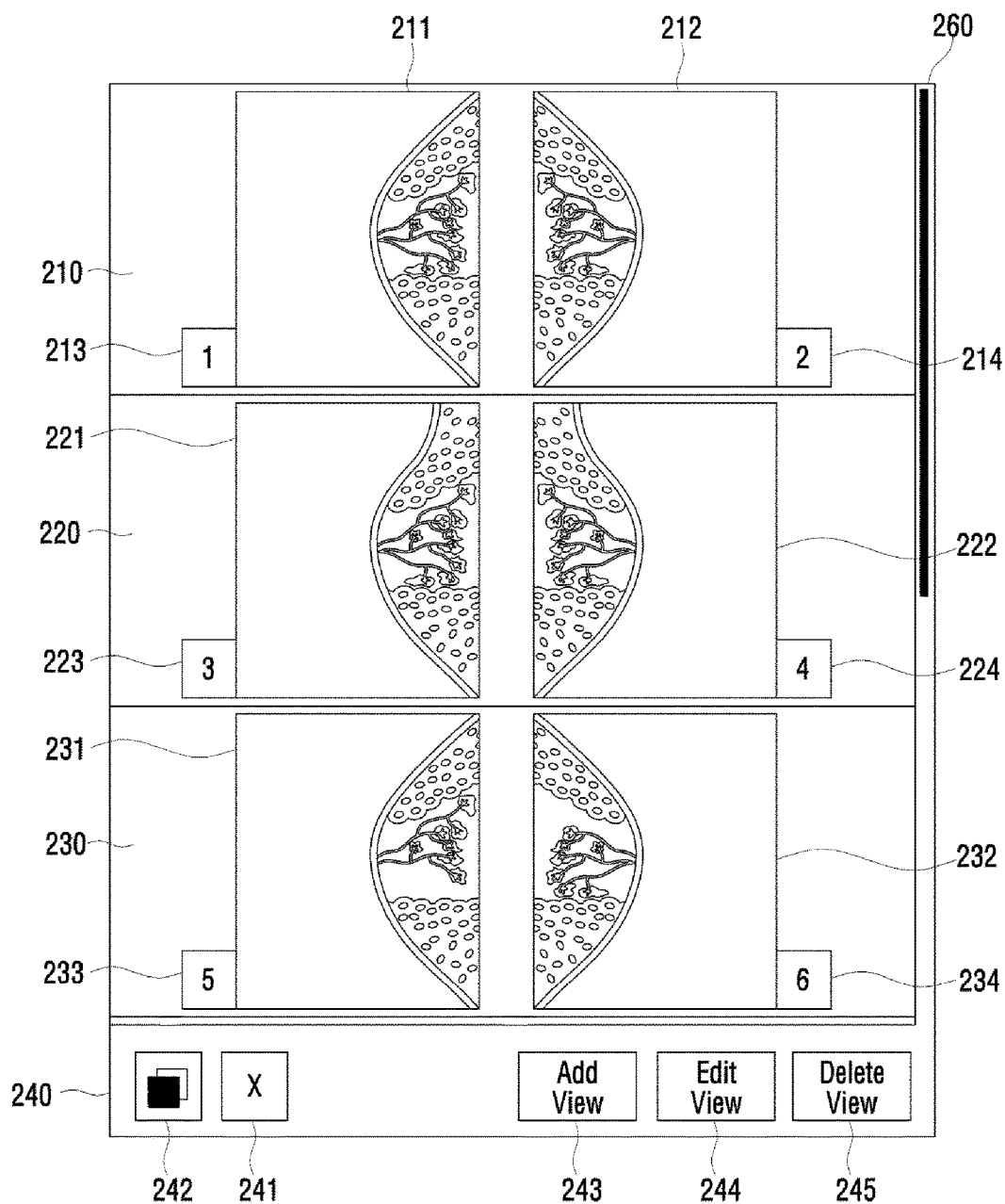
FIGS. 6A to 6B are views illustrating an example of a display unit on which plural radiation images are displayed.
Figure 6B:
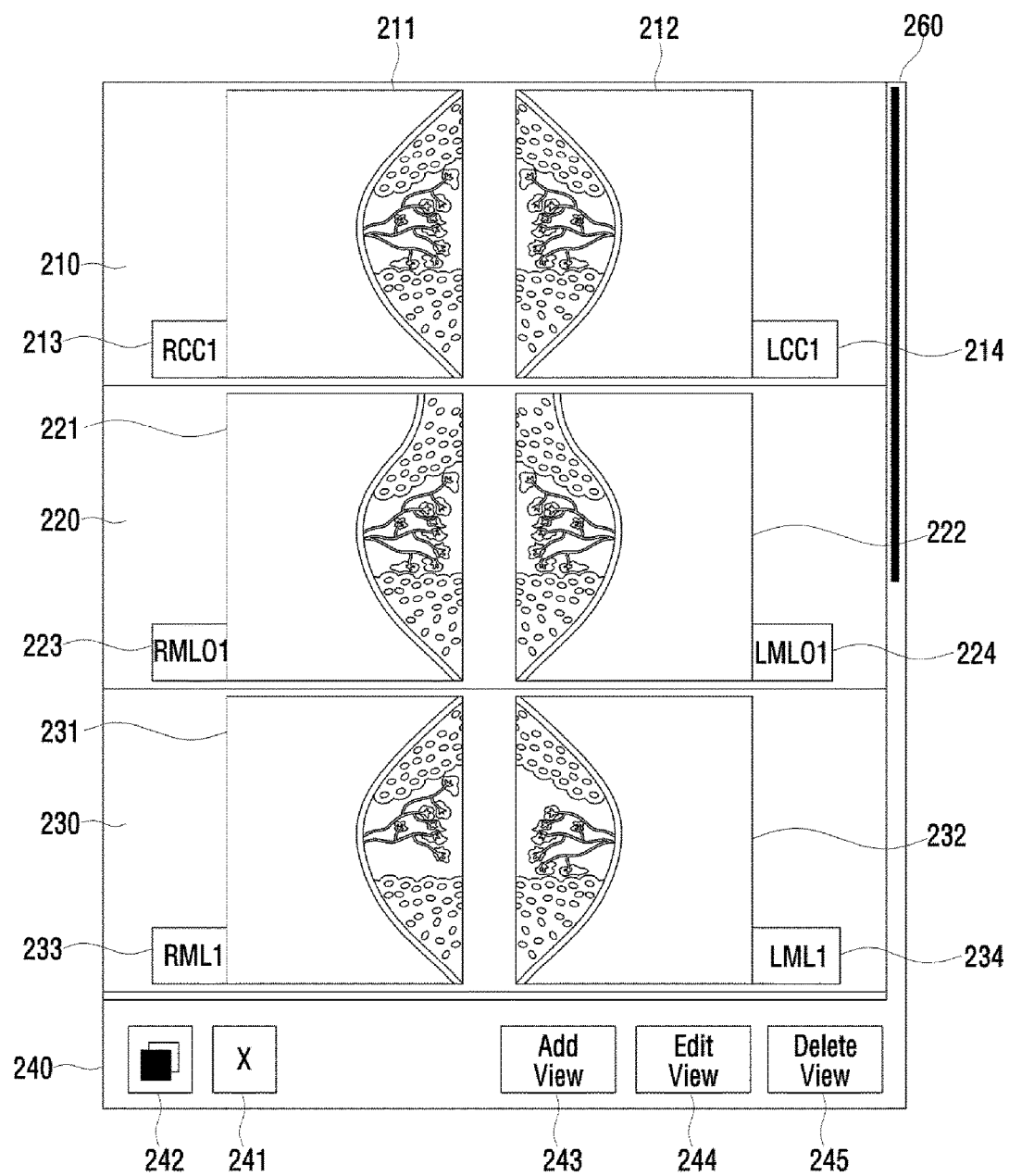

FIGS. 6A to 6B are views illustrating an example of the display unit 160 on which plural radiation images are displayed. FIGS. 6A to 6B illustrate the display unit 160 on which plural radiation images, which were obtained by rotating the radiography module 102 as described above with reference to FIGS. 5A to 5C, are displayed.

As illustrated in FIG. 6A, the display unit 160 may display plural view areas 210, 220 and 230 and a menu area 240. Plural radiation images may be displayed in the view areas. The radiation images displayed in the same view area may correspond to each other. In general, a breast disease is diagnosed by comparing radiation images of both breasts. By displaying the radiation images obtained by taking radiographs of breasts from the same angle in the same view area, diagnosis of a breast disease may be facilitated. The position of the radiation images displayed in the view areas may be predetermined, or may be changed according to user designation.

Referring to FIGS. 6A and 6B, the RCC view 211 and the LCC view 212, i.e., the radiation images obtained by taking radiographs of the right breast 30R and the left breast 30L, each of which may correspond to the object 30, in the craniocaudal direction, may be displayed in the view area 210. The RMLO view 221 and the LMLO view 222, i.e., the radiation images obtained by taking radiographs of the right breast 30R and the left breast 30L, each of which may correspond to the object 30, in the mediolateral oblique direction, may be displayed in the view area 220. The RML view 231 and the LML view 232, i.e., the radiation images obtained by taking radiographs of the right breast 30R and the left breast 30L, each of which may correspond to the object 30, in the mediolateral direction, may be displayed in the view area 230. By displaying the radiation images taken from the same angle at the same height in the same view area, a user may more easily compare the radiation images of both breasts. Further, information about the radiation images may be additionally displayed in the view areas. For example, a name of each radiation image may be displayed. The size of each view area may be fixed according to a predetermined width and height. Alternatively, the width and height of each view area may be changed according to the size of the display unit 160, the size or resolution of the radiation image, or user designation. As shown in FIG. 6A, the view areas may be arranged in terms of rows. However, the disclosure is not so limited, and the view areas may be arranged in terms of columns, for example.

It has been described above that the display unit 160 displays three view areas 210, 220 and 230, however, embodiments are not limited thereto. The number of view areas may be less than three or more than three. The number of view areas displayed on the display unit 160 may be designated by a user, or may be changed according to the resolution and/or size of the display unit 160, for example. In a case that the plural view areas are not completely displayed on the display unit 160, the plural view areas may be partially displayed, and the view areas displayed on the display unit 160 may be determined by user scrolling behavior (e.g., by scrolling horizontally and/or vertically).

The control unit 170 may generate tags by tagging the respective radiation images, and may display the generated tags together with the respective radiation images. For example, as shown in FIG. 6A, the control unit 170 may generate tags by assigning consecutive integers (1 through 6) to the radiation images, and may display both the radiation images and the tags 213, 214, 223, 224, 233 and 234 in the view areas. As shown in FIG. 6B, the tags may also be implemented with numbers and characters. In particular, the tags 213 and 214 may be displayed next to the RCC view 211 and the LCC view 212, respectively. The tags 223 and 224 may be displayed next to the RMLO view 221 and the LMLO view 222, respectively. The tags 233 and 234 may be displayed next to the RML view 231 and the LML view 232, respectively. For example, as shown in FIG. 6B, the characters included in the tags may indicate or identify a type of view taken (e.g., RCC1 may be a shorthand notation or abbreviation for a radiation image taken in the craniocaudal direction).

Various icons to control the radiation imaging apparatus 10 may be displayed in the menu area. For example, as shown in FIGS. 6A and 6B, the menu area 240 may be disposed at a lower portion of the display unit 160. The menu area may be always visible in the display unit, or may be hidden from view and activated or displayed when a user touches a predefined area of the display unit. Further, the menu area 240 may be disposed at other areas of the display unit 160 (e.g., an upper portion, left side portion, right side portion, etc.) A recapture view icon 241, a copy view icon 242, an add view icon 243, an edit view icon 244 and a delete view icon 245 may be displayed in the menu area 240. Other icons may be displayed in the menu area and the disclosure is not limited to those shown in the example embodiments. For example, an icon to control a zooming function may be disposed in the menu area, which may be used to zoom in or out of a selected radiation image. For example, an icon to control a rotating function may be disposed in the menu area, which may be used to rotate a selected radiation image.

If the copy view icon 242 is chosen, the control unit 170 may copy a certain radiation image displayed on the display unit 160, and thus obtain a new radiation image. At this time, the certain radiation image may be an image selected by a user.

If the recapture view icon 241 is chosen, the control unit 170 may execute a process of obtaining a certain radiation image again, and thus obtain a recaptured radiation image. For example, if a user chooses the RCC view and the recapture view icon 241, the control unit 170 may control the radiation imaging apparatus so as to capture the RCC view again. Accordingly, the control unit 170 emits radiation toward an object, detects the radiation passing through the object, and obtains a recaptured radiation image. At this time, the certain radiation image may be a radiation image selected by a user or a radiation image taken last.

If the add view icon 243 is chosen, the control unit 170 may add the pre-stored radiation image to the view area. In particular, the control unit 170 may search a radiation image selected by a user or a pre-stored radiation image corresponding to the view area selected by a user, and may add the searched radiation image to a certain view area. Further, in the case of plural pre-stored radiation images, the control unit 170 may generate a pop-up window so as to enable a user to select a radiation image to be added. For example, the pop-up window may include a folder with the pre-stored radiation images for the user to select from. For example, pre-stored radiation images may be stored in a storage device. For example, the storage may be embodied as a storage medium, such as a nonvolatile memory device, such as a Read Only Memory (ROM), Programmable Read Only Memory (PROM), Erasable Programmable Read Only Memory (EPROM), and flash memory, a USB drive, a volatile memory device such as a Random Access Memory (RAM), a hard disk, floppy disks, a blue-ray disk, or optical media such as CD ROM discs and DVDs, or combinations thereof. However, examples of the storage are not limited to the above description, and the storage may be realized by other various devices and structures as would be understood by those skilled in the art.

If the edit view icon 244 is chosen, the control unit 170 may output a screen to edit the selected radiation image so that a user is enabled to edit the selected radiation image. For example, a user may adjust the contrast of the selected radiation image. In addition, using the screen to edit the radiation image, a user may change the view area in which the selected radiation image is to be displayed, or may change a position at which the selected radiation image is to be displayed in the view area. For example, using the screen to edit the radiation image, a user may move the selected radiation image displayed in the right portion of the view area to be displayed in the left portion, or may move the radiation image displayed in the first view area to be displayed in the second view area.

If the delete view icon 245 is chosen, the control unit 170 may delete a certain radiation image. The control unit 170 may generate a pop-up window to confirm whether a user wants to delete the radiation image. The certain radiation image may be a radiation image selected by a user or a radiation image obtained last. The delete view icon 245 may be deactivated in a specific situation, such as the end of radiography.

The control unit 170 may display a scroll bar 260 on one or more portions of the display unit 160. The control unit 170 may set a view area which is displayed on the display unit 160 according to user manipulation of the scroll bar 260. For example, in a case that the plural view areas are not completely displayed on the display unit 160, the control unit 170 may determine a view area which is displayed on the display unit 160 according to user manipulation of the scroll bar 260. For example, as shown in FIG. 6A, the scroll bar may be disposed on a right side of the display unit 160, and may control scrolling in a vertical direction (e.g., up and down direction). However, the scroll bar may be disposed on a left side of the display unit 160. Also, alternatively, or additionally, a scroll bar may be disposed on an upper or lower side of the display unit 160 to control scrolling in a horizontal (e.g., left and right direction).

Referring back to FIG. 2, the control unit 170 may obtain an additional radiation image according to a user command. The additional radiation image may be one of a recaptured radiation image obtained by taking a radiograph of the object 30 again corresponding to the selected radiation image, a duplicate radiation image obtained by copying the selected radiation image, and a loading radiation image obtained from the pre-stored radiation image corresponding to the selected radiation image. For example, a user may input a command by selecting the recapture view icon 241, the copy view icon 242 and the add view icon 243.

A user command input will now be explained in detail with reference to FIGS. 7A and 7B.

Figure 7A:
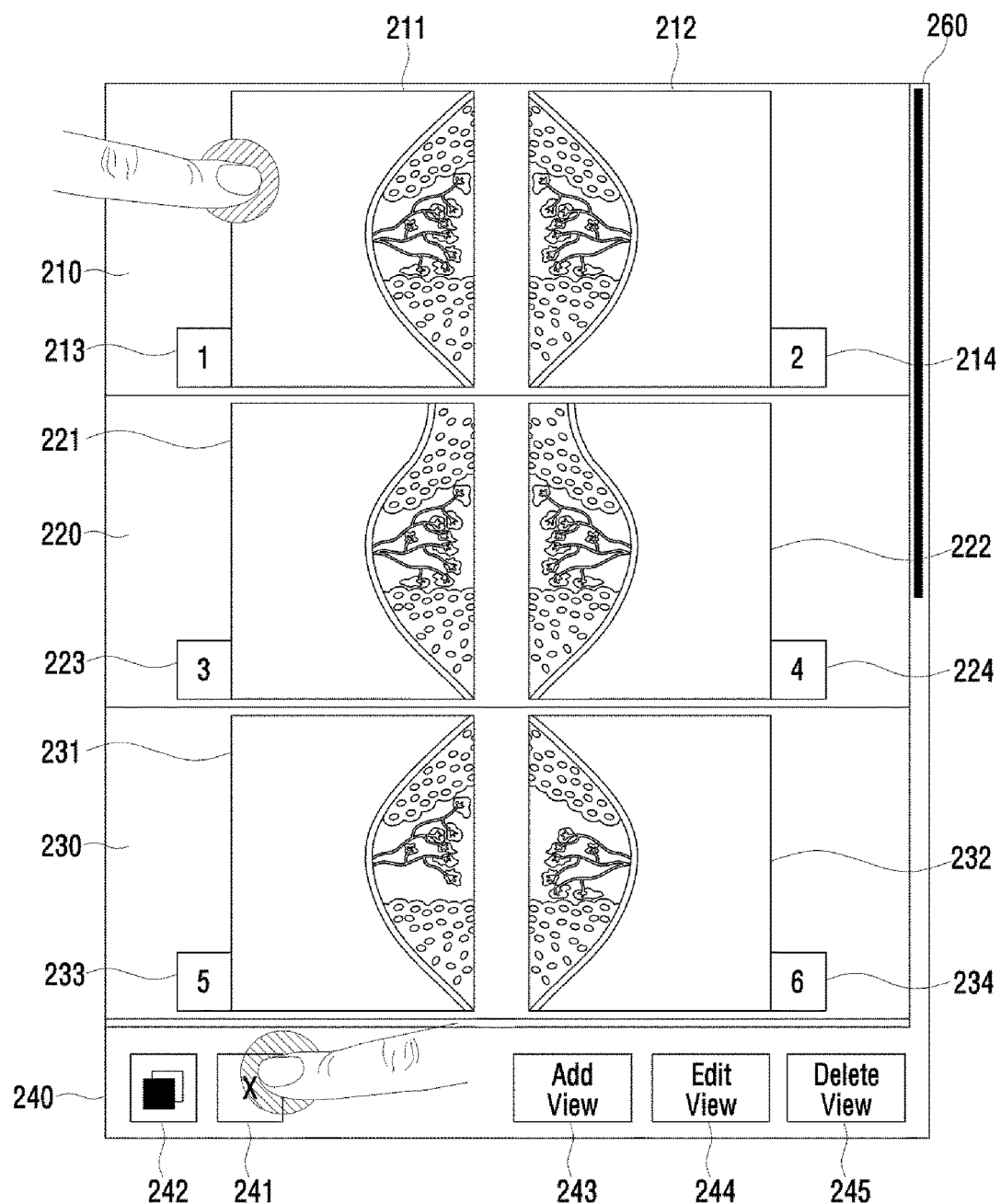
FIGS. 7A to 7B are views to explain an example of receiving a user command input to obtain an additional radiation image.
Figure 7B:
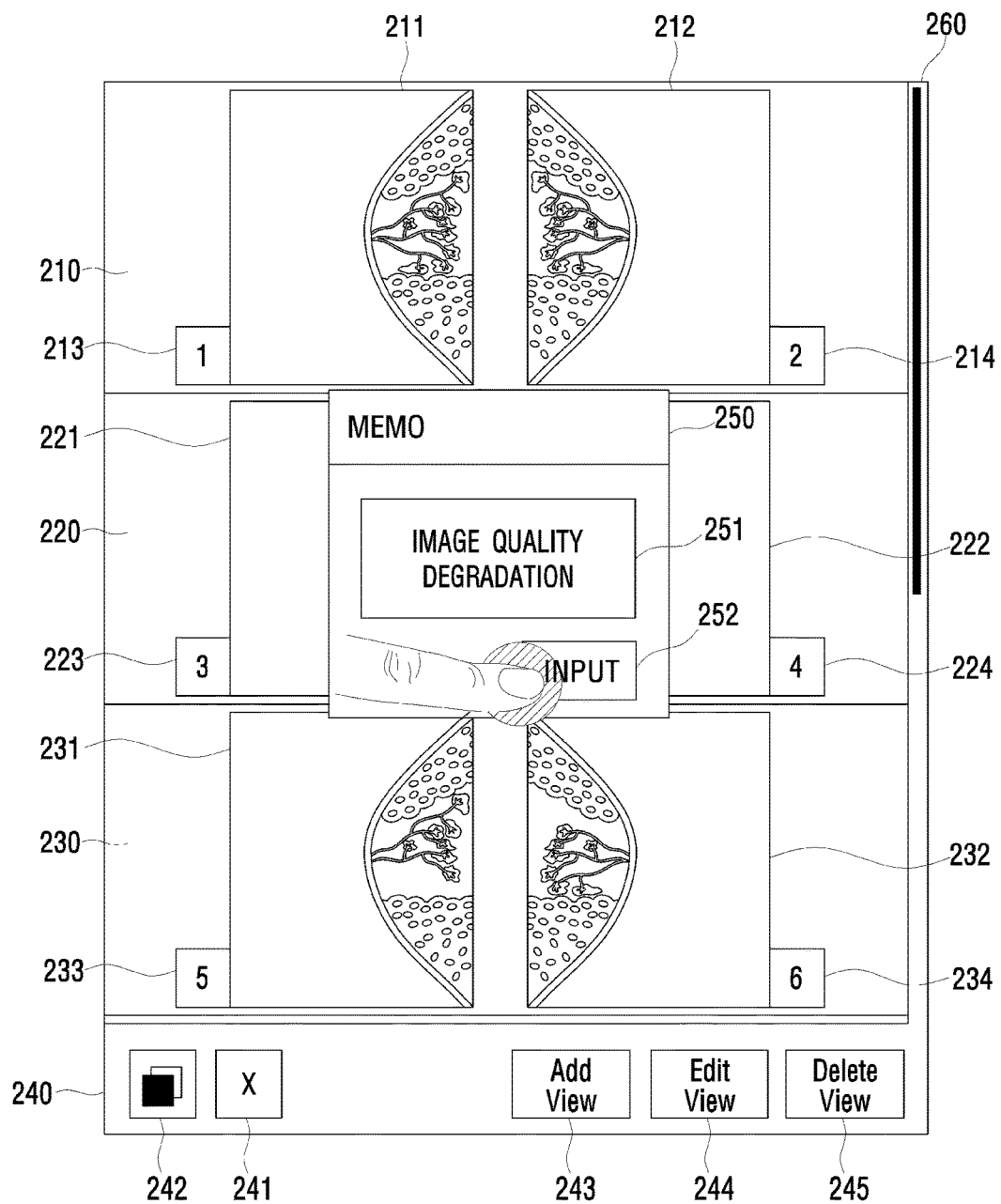

FIGS. 7A and 7B are views to explain an example of receiving a user command input to obtain an additional radiation image. A user may input a command to obtain an additional radiation image. Hereinafter, a process of receiving a user command input to obtain a recaptured radiation image as an example of obtaining an additional radiation image will be described in detail with reference to FIGS. 7A and 7B.

As illustrated in FIG. 7A, a user may select a radiation image to be recaptured by touching the radiation image 211, which needs to be recaptured, of the plural radiation images displayed on the display unit 160. For example, the user may input a touch using a finger, or another object, such as by using a stylus. Then, a user may input a command to obtain a recaptured radiation image by touching the recapture view icon 241 displayed in the menu area 240. Alternatively, the operations may be performed in a reverse order. For example, the user may first touch the recapture view icon 241, and then select the radiation image to be recaptured by touching the radiation image.

If the command to obtain the recaptured radiation image is input, the control unit 170 may generate a pop-up window 250 depicted in FIG. 7B, and may receive information about recaptured radiation image acquisition. For example, the pop-up window 250 may include a text box 251 to receive information about the recaptured radiation image and an input button 252 to store content input to the text box 251.

If the command to obtain the recaptured radiation image is input by a user, the control unit 170 may obtain the recaptured radiation image corresponding to the selected radiation image. In particular, the control unit 170 may rotate the radiography module 102 to a position corresponding to the selected radiation image and recapture a radiation image corresponding to the selected radiation image by compressing the right breast 30R, thereby obtaining the recaptured radiation image.

Figure 8:
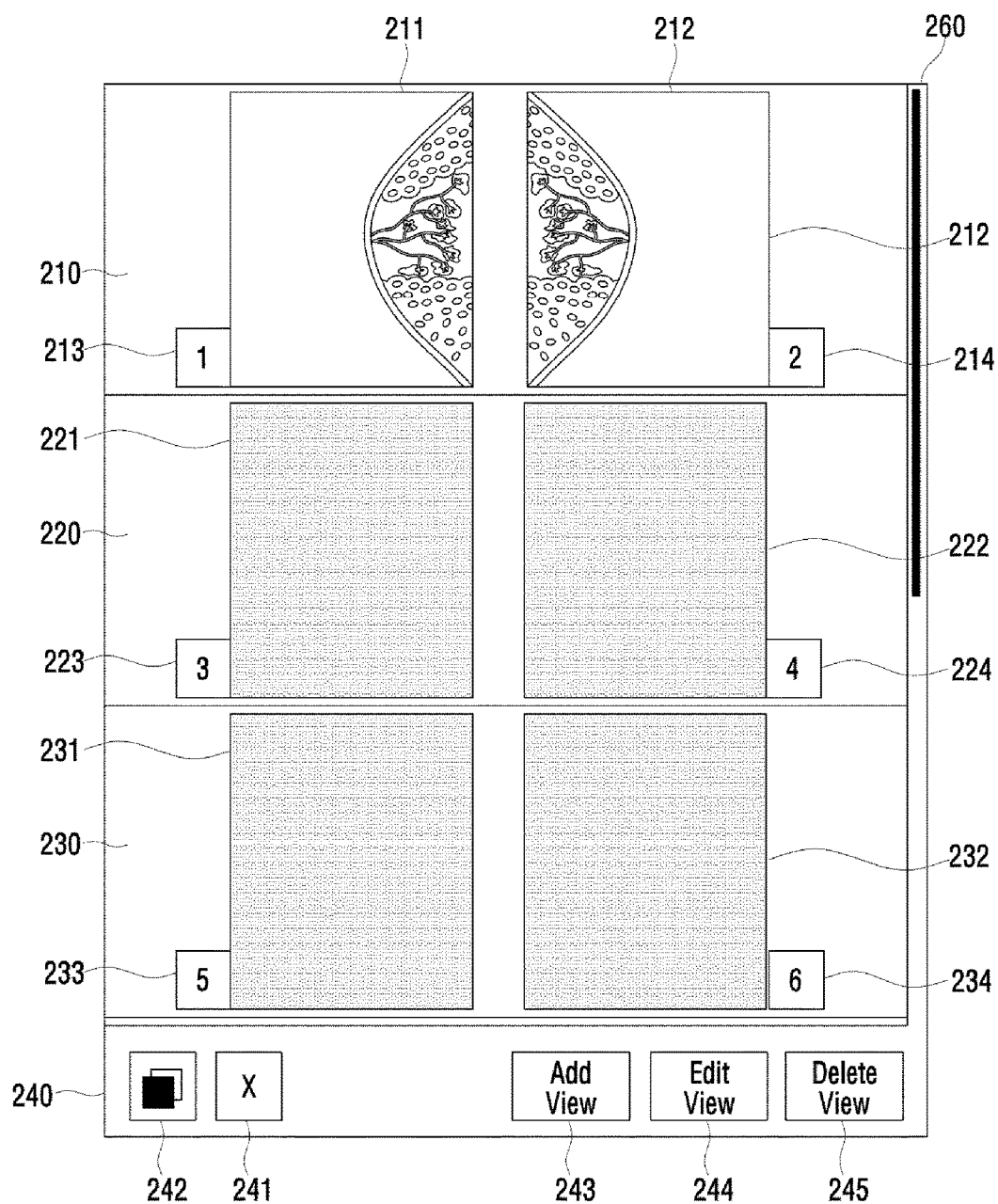
FIG. 8 is a view to explain another example of receiving a user command input to obtain a recaptured radiation image.

FIG. 8 is a view to explain another example of receiving a user command input to obtain the recaptured radiation image. Although the radiation image to be recaptured is not selected by a user, the control unit 170 may obtain the recaptured radiation image corresponding to a certain radiation image. For example, if a user selects the recapture view icon 241, the control unit 170 may recapture a radiation image corresponding to the radiation image obtained last (i.e., the radiation image obtained most recently). As described above with reference to FIGS. 5A to 5C, after the RCC view 211 is first obtained, then the LCC view 212 is obtained by compressing the left breast 30L in the craniocaudal direction by the radiography module 102. Accordingly, the LCC view 212 is displayed, and if a user selects the recapture view icon 241, the control unit 170 obtains the recaptured radiation image corresponding to the LCC view which was obtained last, and displays the obtained recaptured radiation image in the view area 210.

In other words, if the obtained radiation image is displayed on the display unit 160, a user may immediately check if recapturing is necessary. If a user determines that recapturing is necessary and thus touches the recapture view icon 241, the control unit may perform a series of processes to recapture the radiation image which is captured most recently, and obtain again the recaptured radiation image corresponding to the radiation image taken most recently. Accordingly, time and cost for acquisition of the recaptured radiation image may be minimized.

Although FIGS. 7A-7B and 8 illustrate examples of receiving a user command input to obtain an additional radiation image, a method of inputting a command to obtain an additional radiation image is not limited thereto. For example, a user may input a command to obtain an additional radiation image using an input device such as a mouse, a keyboard or the like. Also, a user may input a command to obtain an additional radiation image by gestures, for example, by using the touchscreen. The gestures may be one or more of touch, tap, flick, drag and swipe. Although it has been described above that a command to obtain a recaptured radiation image is input, a command to obtain a duplicate radiation image or an additional radiation image may also be input by the same or similar method.

The aforementioned additional radiation image may be displayed on the display unit 160 in various manners. Display of the additional radiation image will now be explained in detail with reference to FIG. 9.

Figure 9:
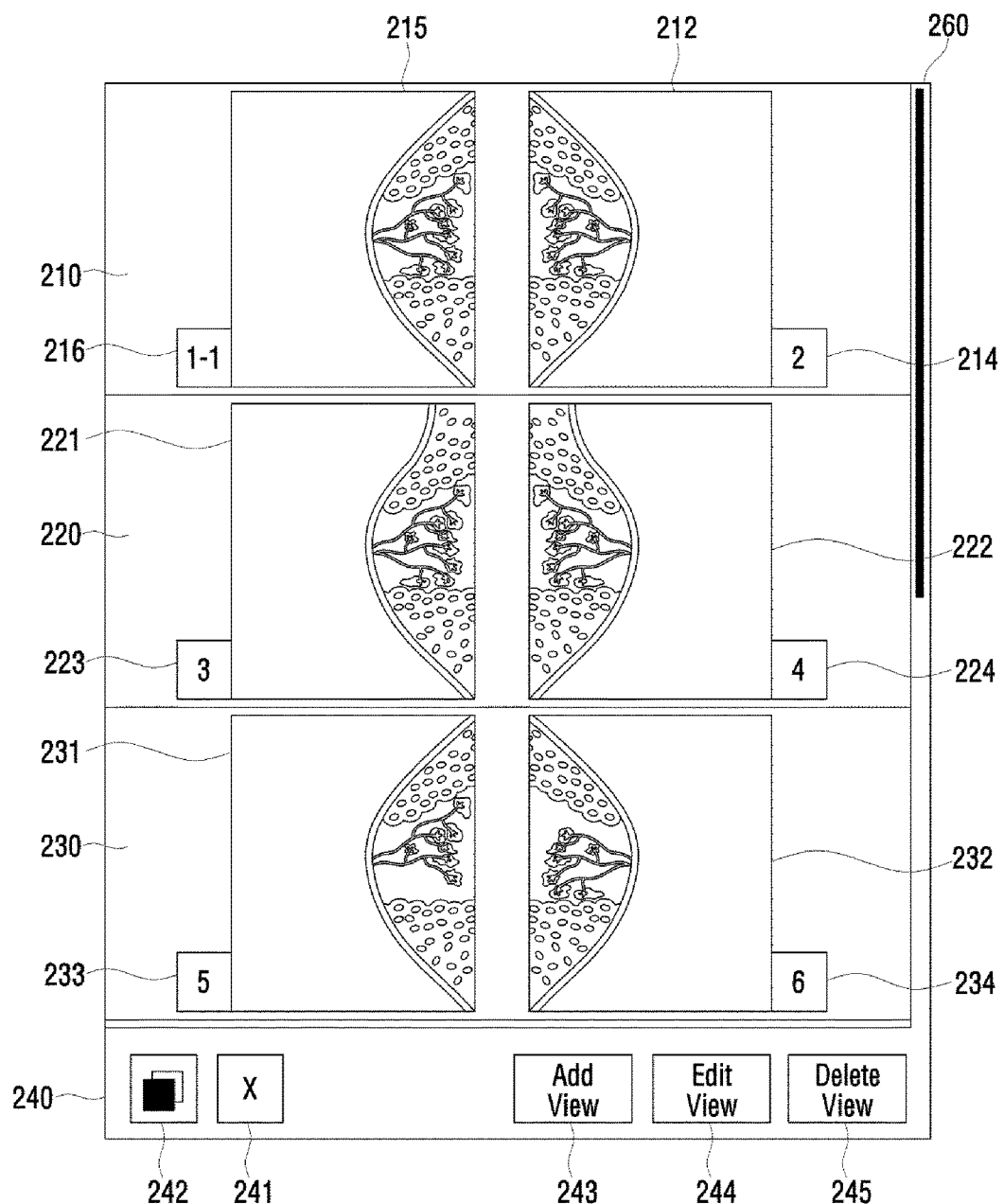
FIG. 9 is a view illustrating an example of the display unit on which an additional radiation image is displayed.

FIG. 9 is a view illustrating an example of the display unit 160 on which the additional radiation image is displayed.

The control unit 170 may replace a certain radiation image which has been displayed previously with the additional radiation image 215 obtained according to a user input, and may display the additional radiation image. The certain radiation image may be a radiation image from which a user selects acquisition of the additional radiation image, or a radiation image taken last.

The control unit 170 may generate a tag 216 with respect to the additional radiation image, and may display the generated tag 216 together with the additional radiation image 215. The tag 216 with respect to the additional radiation image may be different from the tag of the certain radiation image. For example, the control unit may generate a tag in an ascending order corresponding to the tag of the radiation image selected by a user. For example, as shown in FIG. 9, the additional radiation image 215 may have a tag 216 with a numeric identifier of 1-1, which implies a sequential relationship with the corresponding radiation image 211 which has a numeric identifier of 1.

Figure 10A:
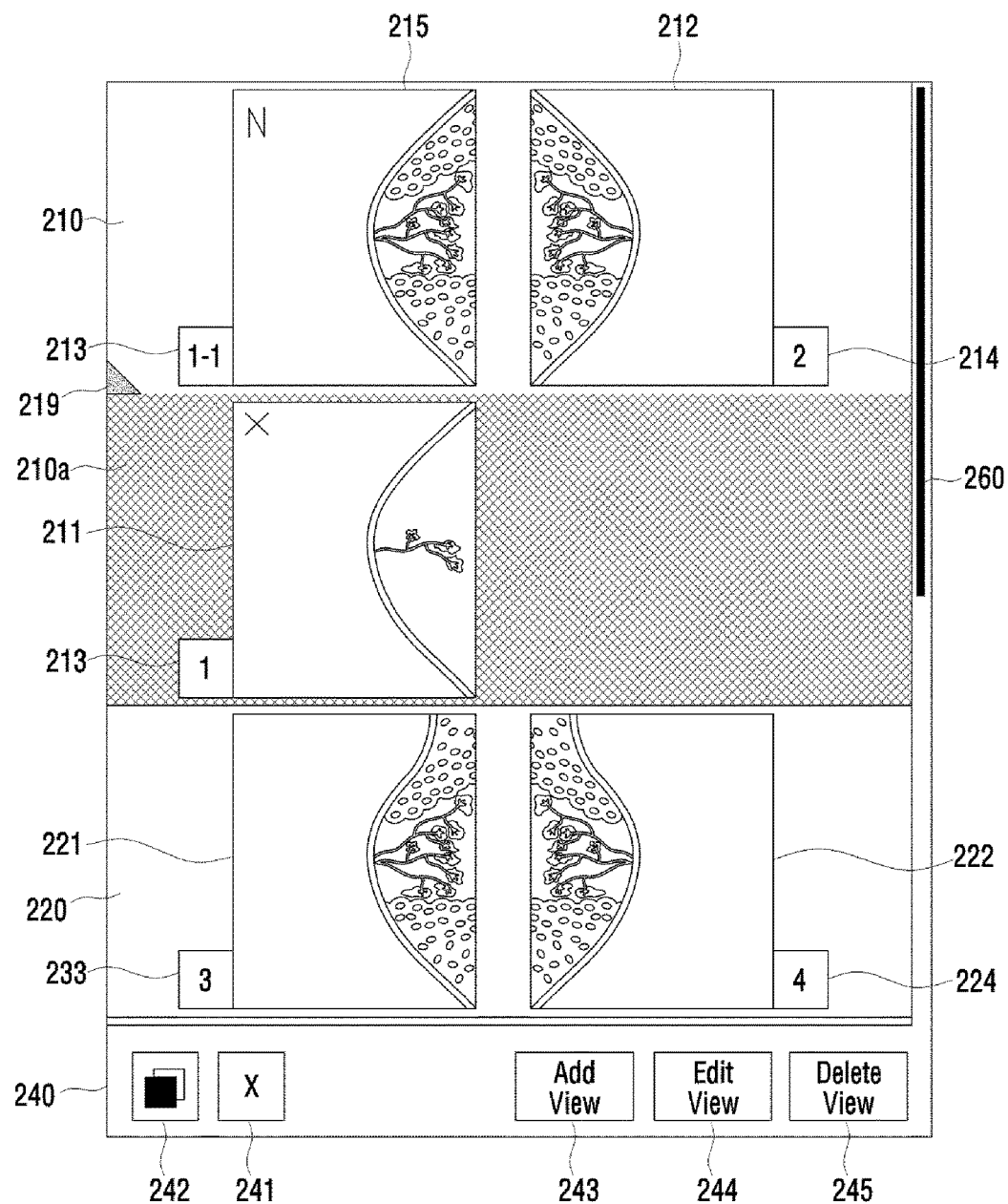
FIGS. 10A to 10D are views illustrating another example of the display unit on which an additional radiation image is displayed.

FIGS. 10A to 10D are views illustrating another example of the display unit 160 on which the additional radiation image is displayed. If a user inputs a command to obtain the recaptured radiation image corresponding to the radiation image 211 as shown in FIG. 7B, the control unit 170 may display the recaptured radiation image obtained by taking a radiograph of the right breast 30R again as shown in FIG. 10A.

As illustrated in FIG. 10A, the control unit 170 may generate an extension area 210a in the view area 210 to extend the view area 210, and may display both the additional radiation image 215 and the radiation image 212 corresponding to the additional radiation image 215 in the extended view area 210.

In particular, the control unit 170 may generate the extension area 210a below the view area 210, in which the radiation image 211 set to obtain the recaptured radiation image is displayed, thereby extending the view area 210.

The extension area 210a may be generated with a predetermined width and/or height, or may have a width and/or height determined according to user designation or input.

The control unit 170 may display the recaptured radiation image 215 in the position where the radiation image 211 has been displayed, and may display the radiation image 211 selected to be recaptured in the extension area 210a.

The radiation images corresponding to each other may be arranged in the same row, and the additional radiation image and the radiation image corresponding thereto may be arranged in the same column, thereby enhancing convenience in using the radiation imaging apparatus 10.

Figure 10B:
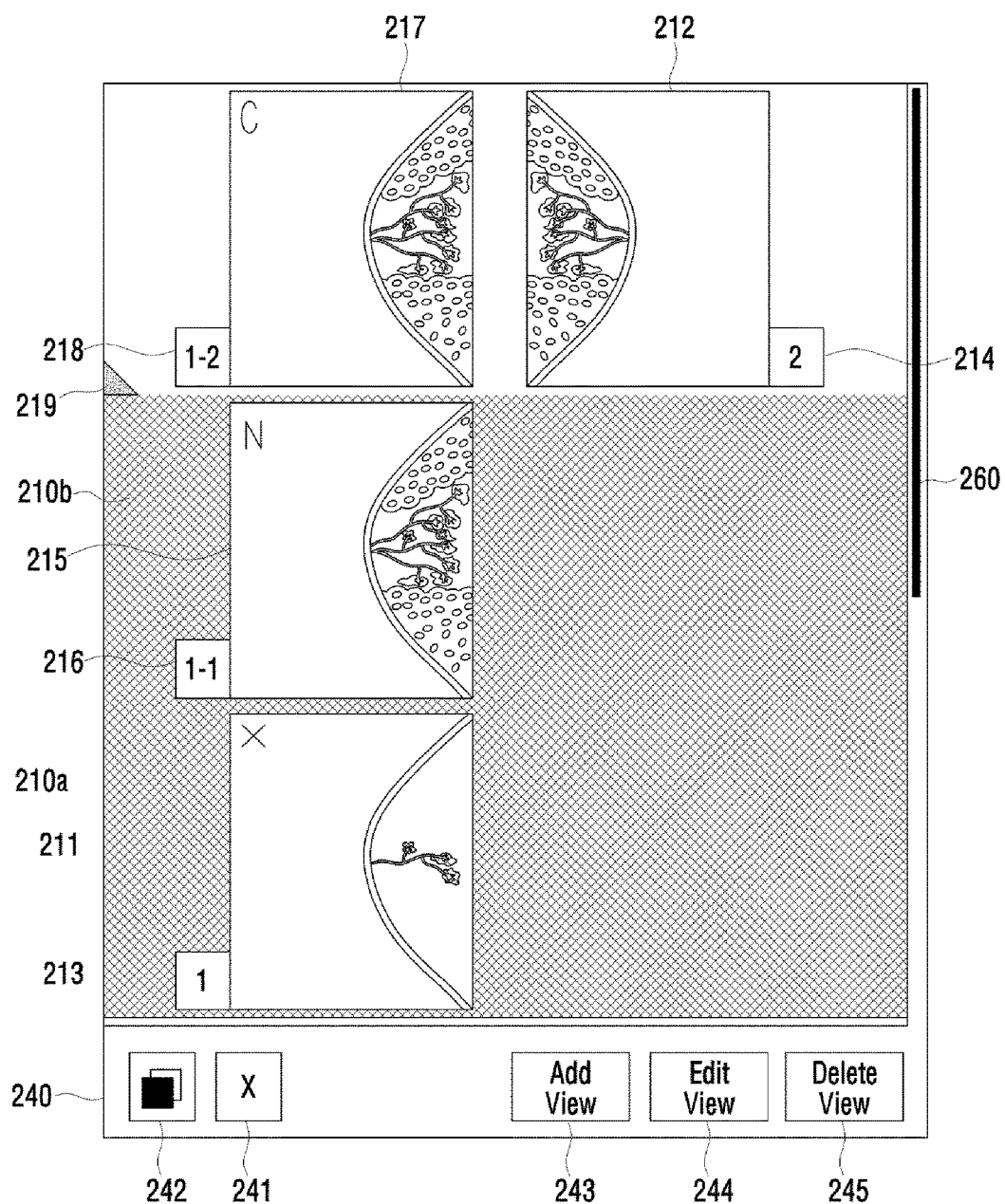

Plural additional radiation images may be generated and input corresponding to one radiation image. For example, when the screen is displayed as shown in FIG. 10A, if a user selects the recaptured radiation image 215 and then selects the copy view icon 242, the control unit 170 copies the recaptured radiation image 215 and obtains a duplicate radiation image 217, as shown in FIG. 10B, for example. Alternatively, a user may first select the copy view icon 242 and then select the recaptured radiation image 215, such that the control unit 170 copies the recaptured radiation image 215 and obtains a duplicate radiation image 217, as shown in FIG. 10B, for example.

As illustrated in FIG. 10B, the control unit 170 may generate an extension area 210b in the view area 210 in which the recaptured radiation image is displayed, may display the recaptured radiation image 215 in the generated extension area 210b, and may display the duplicate radiation image 217 in the position where the recaptured radiation image 215 has been displayed (i.e., was previously displayed). The selected radiation image 211 may be displayed in the generated extension area 210a. Thus, more than one extension area may be generated in the example embodiments.

The control unit 170 may generate tags with respect to the additional radiation images, and may display the generated tags together with the radiation images. The generated tags may correspond to the tag of the selected radiation image.

For example, as illustrated in FIG. 10B, the control unit 170 may generate the tags in the order of 1-1 and 1-2 and so on, according to the order of obtaining the additional radiation images, and may display the additional radiation images 215 and 217 and the tags 216 and 218 together.

By displaying the tags together with the additional radiation images, discrimination between the plural radiation images may be enhanced.

Further, the control unit 170 may generate and display a marker at a portion of the additional radiation image or the radiation image corresponding to the additional radiation image. The marker serves to enable a user to perceive intuitively information about each image, and may include characters or symbols, which are predetermined or designated by a user.

Figure 10C:
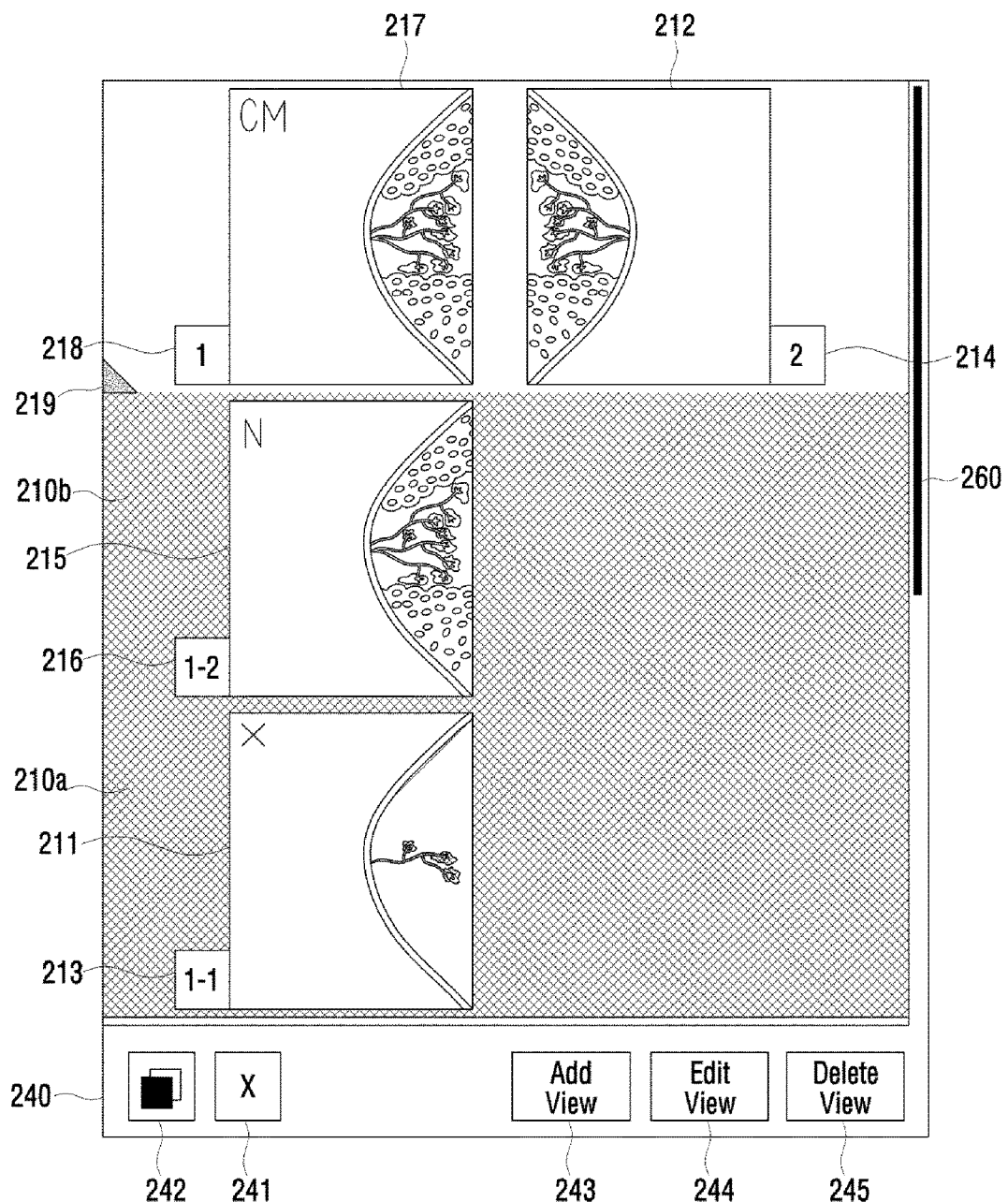

For example, as shown in FIG. 10C, the control unit 170 may generate a marker X for the selected radiation image, a marker N for the recaptured radiation image, a marker C for the duplicate radiation image, a marker A for the loading radiation image, and a marker M for the edited radiation image edited by a user. More than one marker may be displayed per radiation image, for example as shown in FIG. 10C with respect to radiation image 217.

The marker may be displayed at a predetermined position or a position designated by a user. For example, the marker may be displayed in a corner of the radiation image (e.g., upper left corner, lower left corner, etc.). When there is more than one marker to be displayed, the markers may be displayed next to one another, or may be displayed separately. Further, the control unit 170 may analyze the radiation image to search a portion having the same degree of brightness in the radiation image (i.e., a portion of the radiation image which does not include information about the object 30), and may generate the marker at the searched portion. That is, for example, the marker may be set such that it does not overlap on a portion of the radiation image which includes information about the object.

The control unit 170 may further display a fold button 219 in a portion of the view area. The fold button 219 may be configured to (arranged to, adapted to, capable of, suitable for, etc.) receive a user command to display the extension area. The fold button 219 may be displayed only in the view area in which the extension area is generated. For example, as shown in FIGS. 10B and 10C, the fold button 219 may be displayed in a portion of the view area 210 in which the additional radiation image is displayed. For example, the fold button 219 may be displayed in a corner of the view area (e.g., upper left corner, lower left corner, etc.) If a user touches the fold button 219 (or clicks on or otherwise selects the fold button 219), the control unit 170 may not display the extension area 210a as illustrated in FIG. 10D.

Figure 10D:
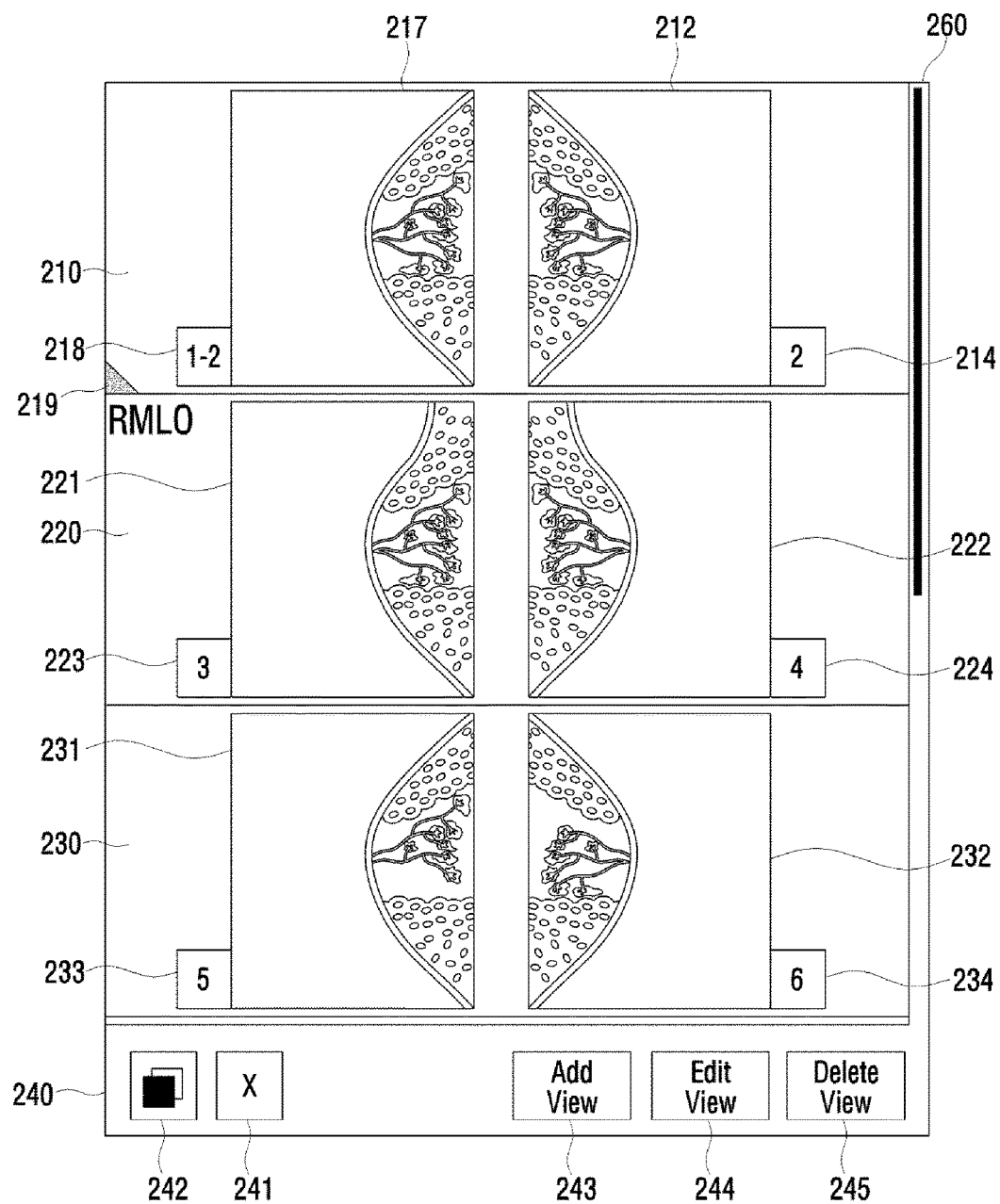

As shown in FIG. 10D, even though the extension area is not displayed, the fold button 219 may be displayed. At this time, if a user touches the fold button 219, the control unit 170 may display the extension area 210a and the radiation image 211 displayed in the extension area as shown in FIGS. 10B and 10C.

A user may adjust the radiation image displayed on the display unit 160. For example, a user may move, edit or delete the radiation image displayed on the display unit 160 using gestures.

Describing with reference to FIG. 10B, if a user touches the recaptured radiation image 215 and drags the recaptured radiation image 215 toward the duplicate radiation image 217, the control unit 170 may switch the display positions of the recaptured radiation image 215 and the duplicate radiation image 217. Accordingly, a user may easily compare the various images.

If a user selects the recaptured radiation image 215 by touching the same and then touches the delete view icon 245, the control unit 170 may delete the recaptured radiation image 215 selected by a user. At this time, the control unit

170 may also delete the extension area 210*a* in which the recaptured radiation image 215 is displayed. If the selected radiation image satisfies a specific condition, the control unit 170 may prevent deletion of the radiation image. For example, if a locking function is set or radiation image acquisition is completed, the radiation image may be prevented from being deleted even when a user touches the delete view icon 245.

If a user selects the duplicate radiation image 217 by touching the same and then touches the edit view icon 244, the control unit 170 may output an edit interface which enables a user to edit the duplicate radiation image 217. The user may edit a radiation image using various tools to change, alter, or edit various attributes of the radiation image (e.g., by editing the brightness, contrast, cropping the radiation image, changing a size of the radiation image, etc.). The edit interface may be a pre-stored interface. When a user finishes editing the duplicate radiation image 217, the control unit 170 may display the edited duplicate radiation image 217. As shown in FIG. 10C, a marker (e.g., M), which represents that the duplicate radiation image 217 is edited, may be displayed in a portion of the duplicate radiation image 217.

If a user changes the view area in which the radiation image will be displayed or a portion of the view area in which the radiation image will be displayed using the edit interface, the display unit 160 may display the selected radiation image in the view area or in the portion of the view area which is changed according to a user input.

Hereinafter, a radiation image display method will be described in detail with reference to FIGS. 11 through 13.

Figure 11:
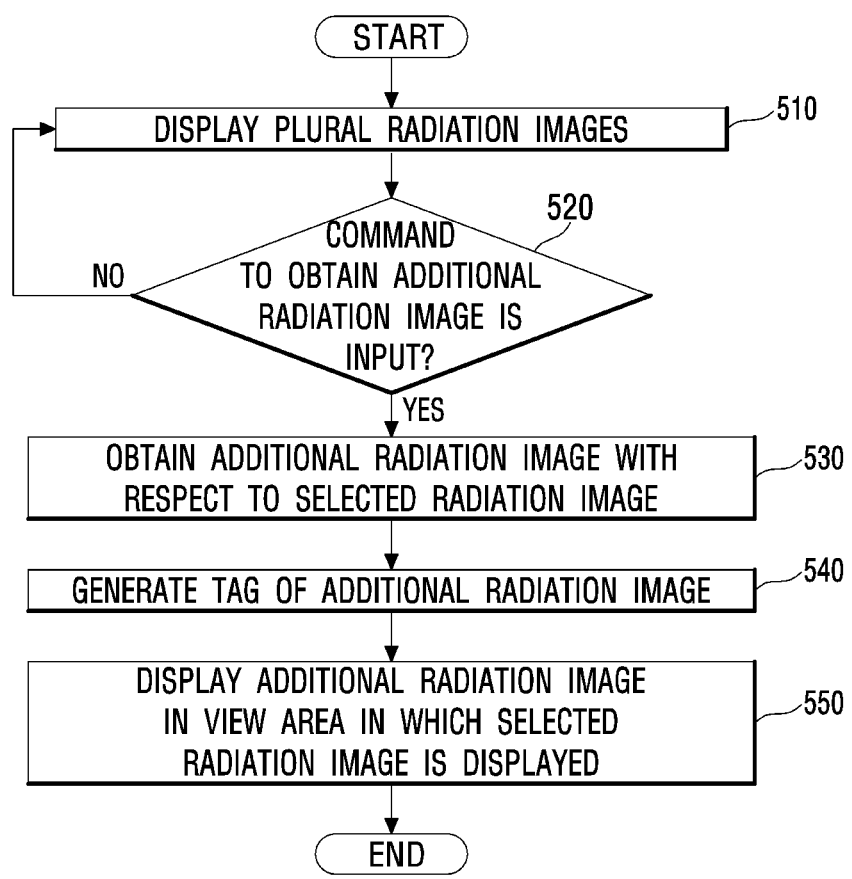
FIG. 11 is a flowchart to explain an example of a radiation image display method.

FIG. 11 is a flowchart to explain an example of a radiation image display method. Referring to FIG. 11, the control unit 170 obtains plural radiation images, and displays the obtained plural radiation images on the display unit 160 at operation 510.

The radiation images may be obtained as described above with reference to FIGS. 5A-5C, and the radiation images may be displayed as described above with reference to FIGS. 6A-6B.

For example, whenever the radiation images are obtained, the control unit 170 may determine the view areas in which the radiation images will be displayed, and may display the radiation images in the determined view areas. At this time, the view areas, in which the respective radiation images will be displayed, may be determined according to a preset criterion, or may be selected according to a user input.

The shape, size and number of view areas to display the radiation images may be previously set.

The control unit 170 may generate tags by tagging the respective radiation images, and may display the generated tags together with the respective radiation images. The tags may be generated without being overlapped on the radiation image. Alternatively, the tags may be generated and be overlapped on the radiation image, and may be displayed in a transparent manner, or in an area of the radiation image which does not include information about the object.

The control unit 170 determines whether a command to obtain an additional radiation image is input at operation 520. The command to obtain the additional radiation image may be input by various methods. For example, the command may be input by an input device, such as a mouse, a keyboard or the like, or via a user's gestures.

As described above with reference to FIGS. 7A-7B, a user may input a command to obtain the additional radiation image by touching the display unit 160 on which plural radiation images are displayed. The command to obtain the additional radiation image may be input before the plural radiation images with respect to the object are totally obtained. In other words, a user may first check the respective obtained radiation images, and then may input the command to obtain the additional radiation image if recapturing is necessary. Accordingly, time for acquisition of the recaptured radiation image may be reduced, and inconvenience of patients may be minimized.

If the command to obtain the additional radiation image is not input (NO at operation 520), the control unit 170 continuously obtains the radiation images and displays the obtained radiation images according to a preset program or user manipulation at operation 510.

If the command to obtain the additional radiation image is input (YES at operation 520), the control unit 170 obtains the additional radiation image with respect to the selected radiation image at operation 530. The additional radiation image may be varied by a user input. In particular, the additional radiation image may be one or more of a recaptured radiation image obtained by taking a radiograph of the object 30 again corresponding to the selected radiation image, a duplicate radiation image obtained by copying the selected radiation image, and a loading radiation image obtained from the pre-stored radiation image corresponding to the selected radiation image.

The control unit 170 generates a tag of the additional radiation image at operation 540. The tag of the additional radiation image may be generated based on the selected radiation image. For example, the tag may be generated in an ascending order corresponding to the tag of the selected radiation image.

The control unit 170 displays the additional radiation image in the view area in which the selected radiation image is displayed at operation 550. For example, the control unit 170 may display the additional radiation image by replacing the selected radiation image as described above with reference to FIG. 9, or may display both the selected radiation image and the additional radiation image in the extended view area as described above with reference to FIG. 10A.

The radiation images displayed according to the example embodiments may be thumbnail images. The radiation images may be of various formats, including a digital image having a format such as JPEG, GIF, TIFF, PNG, raw image format, and the like. The selected radiation image may include a radiation image selected according to a user input or a radiation image satisfying a specific condition.

Figure 12:
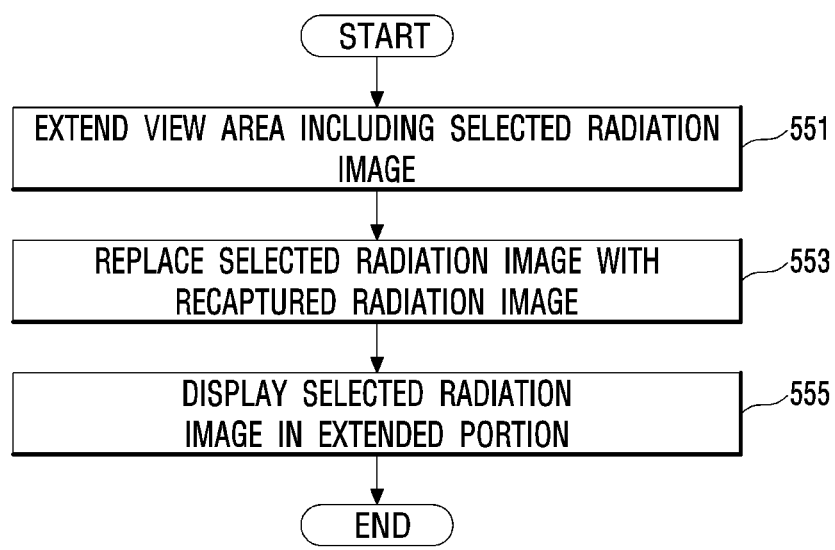
FIG. 12 is a flowchart to explain an example of an additional radiation image display method.

FIG. 12 is a flowchart to explain an example of an additional radiation image display method. A screen on which the radiation images are displayed by the display method will be explained with reference to FIGS. 10A and 12.

The control unit 170 extends the view area in which the selected radiation image is included at operation 551. For example, as shown in FIG. 10A, the control unit 170 generates the extension area 210*a* below the view area 210, in which the radiation image 211 set to obtain the recaptured radiation image is displayed, thereby extending the view area 210.

The extension area 210*a* may be generated with a predetermined width and/or height, or may have a width and/or height determined according to a user designation or input.

The control unit 170 replaces the selected radiation image with the additional radiation image at operation 553, and displays the selected radiation image in the extended portion at operation 555.

For example, as shown in FIG. 10A, the control unit 170 may display the recaptured radiation image 215 in the position where the radiation image 211 has been displayed, and may display the radiation image 211 selected to be recaptured in the extension area 210*a*.

As shown in FIGS. 10A-10D, the radiation images corresponding to each other may be arranged in the same row, and the additional radiation image and the radiation image corresponding thereto may be arranged in the same column, thereby enhancing convenience in using the radiation imaging apparatus 10. Alternatively, the radiation images corresponding to each other may be arranged in the same column, and the additional radiation image and the radiation image corresponding thereto may be arranged in the same row.

The order of displaying the additional radiation image and the selected radiation image may be changed according to a user input.

Figure 13:
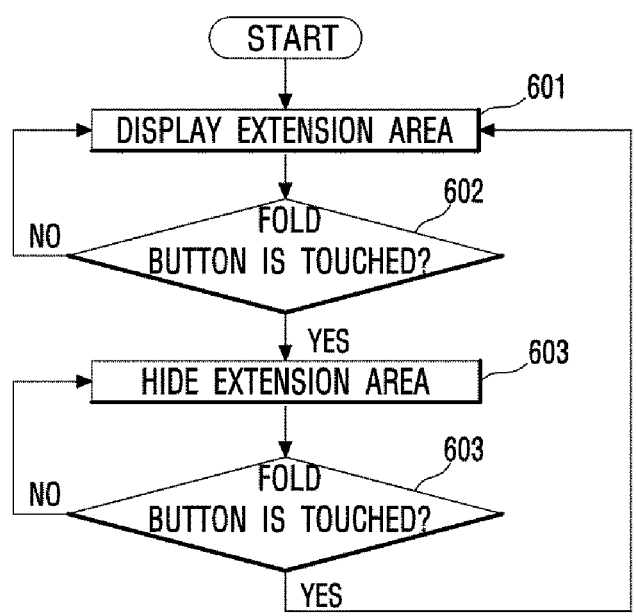
FIG. 13 is a flowchart to explain a method of hiding an extension area.

FIG. 13 is a flowchart to explain a method of hiding the extension area. As illustrated in FIGS. 10A-10D, the fold button may be displayed in a portion of the view area in which the extension area is generated.

Further, the control unit 170 may generate a tag with respect to the additional radiation image and display the tag together with the additional radiation image, or may display certain markers at a portion of the additional radiation image and the selected radiation image. The tag and marker may be generated and displayed according to the above-described method. Alternatively, the tag and marker may be generated and displayed together at a portion of the additional radiation image, or displayed together at a portion of the view area outside of the radiation image.

In a state that the extension area is displayed at operation 601, if a user touches the fold button (YES at operation 602), the control unit 170 hides the extension area at operation 603. In particular, the extension area generated in the view area and the radiation image displayed in the extension area are prevented from being displayed on the display unit 160.

For example, as shown in FIGS. 10B and 10C, the fold button 219 may be displayed at a portion of the view area 210 in which the additional radiation image is displayed. At this time, if a user touches the fold button 219, the control unit 170 may not display the extension area 210*a* as shown in FIG. 10D.

In a state that the extension area is hidden at operation 603, if a user touches the fold button (YES at operation 604), the control unit 170 displays the hidden extension area. In particular, the control unit 170 displays the extension area and the selected radiation image displayed in the extension area.

The fold button 219 may also be displayed at a portion in which the extension area is not displayed as shown in FIG. 10D. At this time, if a user touches the fold button 219, the control unit 170 may display the extension area 210*a* and the radiation image 211 displayed in the extension area as shown in FIGS. 10B and 10C.

Figure 14:
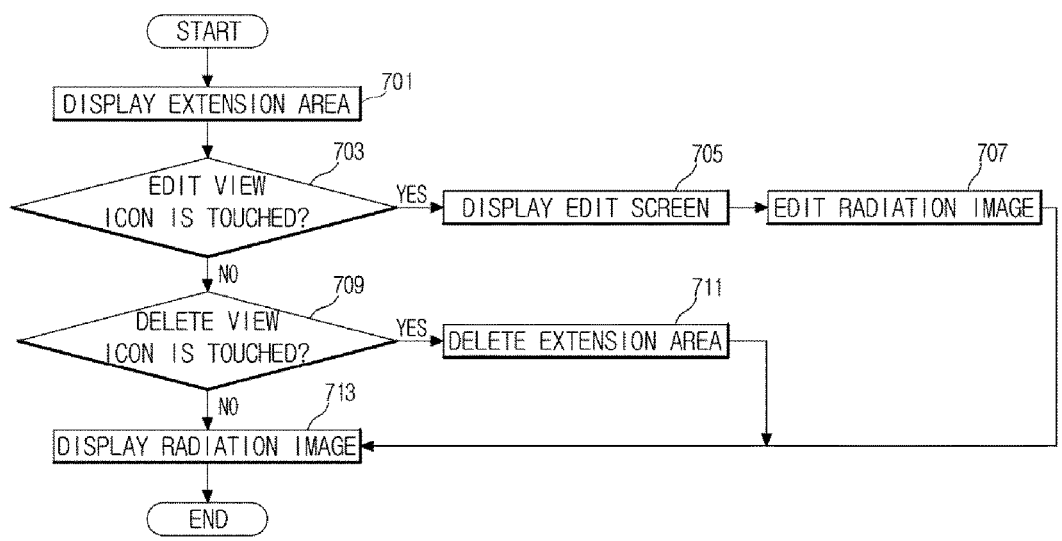
FIG. 14 is a flowchart to explain an example of radiation image adjustment.

FIG. 14 is a flowchart to explain an example of radiation image adjustment.

Referring to FIGS. 14 and 10A to 10D, the display unit 160 may display plural radiation images. A user is enabled to manipulate the plural radiation images displayed on the display unit 160 in various ways.

First, a user may select a radiation image to be manipulated at operation 701. For example, a user may touch a specific radiation image displayed on the display unit 160 to select the same.

If a user touches the edit view icon 244 (YES at operation 703), the control unit 170 displays a screen to edit the selected radiation image at operation 705. At this time, the screen to edit the radiation image may be a pre-stored screen (e.g., a pop-up window). In an alternative embodiment the user may first touch the edit view icon 244 and then touch a radiation image to select that radiation image as the one to be edited.

A user edits the selected radiation image through the screen to edit the radiation image at operation 707. If a user finishes editing, the control unit 170 replaces the selected radiation image with the edited radiation image and displays the edited radiation image at operation 713.

If a user touches the delete view icon 245 (YES at operation 709), the control unit 170 deletes the extension area at operation 711, and displays the radiation image again at operation 713. The deleted extension area is the extension area generated in the view area in which the selected radiation image is displayed.

Aspects of the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although example embodiments of the disclosure have been shown and described, it would be appreciated by those skilled in the art that changes may be made to these example embodiments without departing from the principles and spirit of the disclosure, the scope of which is defined in the claims and their equivalents.

What is claimed is:

1. A radiation imaging apparatus comprising:
   a display unit configured to display, in a first view area, a first radiation image of an object captured from a first angle, and to display, in a second view area, a second radiation image of the object captured from a second angle different from the first angle; and
   a control unit configured:
   to receive an input in the first view area selecting the first radiation image,
   in response to the input selecting the first radiation image being received and an input to obtain a recaptured image, to obtain a third radiation image of the object that is different from and corresponds to the selected first radiation image by controlling the radiation imaging apparatus to move to a position corresponding to the first angle of the first radiation image, based on information included in the selected first radiation image, and recapture the selected first radiation image as the third radiation image, the third radiation image being captured from the first angle after the input selecting the first radiation image is received, and to control the display unit to display the third radiation image in substitution for the first radiation image in the first view area in which the selected first radiation image is displayed, by replacing the first radiation image with the third radiation image, wherein the display unit displays an extension area in the first view area between the third radiation image displayed in the first view area and the second view area, wherein the display unit displays the selected first radiation image in the displayed extension area, and wherein the display unit displays the first radiation image and the second radiation image in a different row.

2. The radiation imaging apparatus according to claim 1, wherein the display unit does not display the extension area when the control unit receives an input to delete the selected radiation image displayed in the extension area.

3. The radiation imaging apparatus according to claim 1, wherein the display unit displays a fold button to receive an input to display or hide the extension area, the fold button being displayed at a portion of the first view area in which the extension area is generated.

4. The radiation imaging apparatus according to claim 1, wherein the control unit obtains the third radiation image by controlling a radiography module to take a radiograph of the object again from the first angle.

5. The radiation imaging apparatus according to claim 1, wherein the control unit displays plural first radiation images corresponding to each other in the first view area.

6. The radiation imaging apparatus according to claim 5, wherein the plural first radiation images corresponding to each other include radiation images obtained by taking a radiograph of objects corresponding to each other from the same angle.

7. The radiation imaging apparatus according to claim 1, wherein the control unit generates a first tag corresponding to the first radiation image and generates a second tag corresponding to the second radiation image, and controls the display unit to display the first tag with the first radiation image and to display the second tag with the second radiation image.

8. A radiation image display method comprising:
displaying, in a first view area, a first radiation image of an object captured from a first angle;
displaying, in a second view area, a second radiation image of the object captured from a second angle different from the first angle;
receiving an input in the first view area selecting the first radiation image;
obtaining, in response to receiving the input selecting the first radiation image and an input to obtain a recaptured image, a third radiation image of the object that is different from and corresponds to the selected first radiation image by controlling a radiation imaging apparatus to move to a position corresponding to the first angle of the first radiation image, based on information included in the selected first radiation image, and recapture the selected first radiation image as the third radiation image, the third radiation image being captured from the first angle after receiving the input selecting the first radiation image;

displaying the third radiation image in substitution for the first radiation image in the first view area in which the selected first radiation image is displayed, by replacing the first radiation image with the third radiation image;
displaying an extension area in the first view area between the third radiation image displayed in the first view area and the second view area,
displaying the selected first radiation image in the extension area; and
displaying the first radiation image and the second radiation image in a different row.

9. The radiation image display method according to claim 8, further comprising determining whether to display or hide the extension area according to a user input.

10. A radiation imaging apparatus, comprising:
a display unit configured to display a plurality of radiation images;
a radiography module including a radiation source configured to emit radiation toward an object, and a radiation detector configured to detect radiation that has passed through the object and to output electric signals corresponding to the detected radiation;
a radiation module driving unit configured to rotate the radiography module; and
a control unit configured:
to control the radiation module driving unit to control rotation of the radiography module to obtain radiation images of the object at different angles,
to control the radiation source to emit radiation toward the object,
to obtain the plurality of radiation images based on the electric signals output by the radiation detector, and
to control the display unit to display the plurality of radiation images,
wherein
the display unit is configured to display a plurality of view areas including a first view area which includes a first radiation image of the object obtained at a first angle, and a second view area which includes a second radiation image of the object obtained at a second angle, and
the control unit is further configured:
to receive an input selecting the first radiation image,
in response to the input in the first view area selecting the first radiation image and an input to obtain a recaptured image, to obtain a different radiation image that corresponds to the selected first radiation image by controlling, after the input selecting the first radiation is received, the radiography module to move to a position corresponding to the first angle of the first radiation image, based on information included in the selected first radiation image and to emit radiation toward the object to obtain the different radiation image at the first angle,
to control the display unit to display the different radiation image in substitution for the first radiation image in the first view area in which the selected first radiation image is displayed, by replacing the first radiation image with the second radiation image,
to control the display unit to display an extension area in the first view area between the different radiation image displayed in the first view area and the second view area,
to control the display unit to display the first radiation image in the displayed extension area in the first view area, and to control the display unit to display the first radiation image and the second radiation image in a different row.

11. The radiation imaging apparatus according to claim 10, wherein the display unit displays a menu area including a plurality of icons used to control operations of the radiation imaging apparatus, wherein, in response to selection of the first radiation image and a first icon among the plurality of icons displayed in the menu area, the control unit controls the radiation module driving unit to rotate the radiography module to the first angle to obtain the different radiation image at the first angle.

12. The radiation imaging apparatus according to claim 11, wherein, in response to selection of the different radiation image and a second icon among the plurality of icons displayed in the menu area, the control unit controls the radiation imaging apparatus to copy the different radiation image, wherein the control unit generates a second extension area in the first view area, and controls the display unit to display the copy of the different radiation image in the first view area, to display the different radiation image in the first extension area, and to display the first radiation image in the second extension area.

13. The radiation imaging apparatus according to claim 12, wherein the control unit generates different markers for the copy of the different radiation image, the different radiation image, and the first radiation image, the markers being displayed at predetermined positions of the respective radiation images.

\* \* \* \* \*